United States Patent
Reddy et al.

(10) Patent No.: US 6,667,346 B2
(45) Date of Patent: Dec. 23, 2003

(54) METHOD FOR PROTECTING CELLS AND TISSUES FROM IONIZING RADIATION TOXICITY WITH α, β UNSATURATED ARYL SULFONES

(75) Inventors: E. Premkumar Reddy, Villanova, PA (US); M. V. Ramana Reddy, Upper Darby, PA (US); Stephen C. Cosenza, Vorhees, NJ (US); Lawrence Helson, Quakertown, PA (US)

(73) Assignees: Temple University - Of The Commonwealth System of Higher Education, Philadelphia, PA (US); Onconova Therapeutics, Inc., Lawrenceville, NJ (US)

( * ) Notice: Subject to any disclaimer, the term of this patent is extended or adjusted under 35 U.S.C. 154(b) by 0 days.

(21) Appl. No.: 10/085,745

(22) Filed: Feb. 28, 2002

(65) Prior Publication Data

US 2003/0060505 A1 Mar. 27, 2003

Related U.S. Application Data

(60) Provisional application No. 60/271,990, filed on Feb. 28, 2001.

(51) Int. Cl.[7] ............................................. A61K 31/10
(52) U.S. Cl. ................... 514/710; 514/709; 514/520; 514/277; 514/439; 514/461; 514/372; 514/408
(58) Field of Search ................................. 514/709, 710, 514/520, 277, 437, 461, 372, 408

(56) References Cited

U.S. PATENT DOCUMENTS 6,359,013 B1 * 3/2002 Reddy et al. ................ 514/709
6,486,210 B2    11/2002 Reddy et al. ................ 514/708
2002/0048798 A1 * 4/2002 Avery et al. ................. 435/183
2002/0055530 A1 * 5/2002 Neuberger et al. ........... 514/381

FOREIGN PATENT DOCUMENTS

WO    WO 00/57872    10/2000
WO    WO 00/59495    10/2000

OTHER PUBLICATIONS

Lazarus et al, J. Hematotherapy, vol. 2, No. 4, pp. 457–466, 1993.*

U.S. patent application Ser. No. 09/689,281, filed Oct. 11, 2000 of Stephen C. Cosenza, M.V. Ramana Reddy and E. Premkumar Reddy for "Method for Protecting Normal Cells From Cytotoxicity of Chemotherapeutic Agents".

Pub–Med 9734697, Abstracting Griggs JJ., "Reducing the Toxicity of Anticancer Therapy: New Strategies", Leuk Res 1998 May;22 Suppl 1:S27–33.

* cited by examiner

*Primary Examiner*—James H Reamer
(74) *Attorney, Agent, or Firm*—Drinker Biddle & Reath LLP

(57) ABSTRACT

Pre-treatment with α,β unsaturated aryl sulfones protects normal cells from the toxic side effects of ionizing radiation. Administration of a radioprotective α,β unsaturated aryl sulfone compound to a patient prior to anticancer radiotherapy reduces the cytotoxic side effects of the radiation on normal cells. The radioprotective effect of the α,β unsaturated aryl sulfone allows the clinician to safely increase the dosage of anticancer radiation. In some instances, amelioration of toxicity following inadvertent radiation exposure may be mitigated with administration of α,β unsaturated arylsulfone.

40 Claims, 6 Drawing Sheets

METHOD FOR PROTECTING CELLS AND TISSUES FROM IONIZING RADIATION TOXICITY WITH α, β UNSATURATED ARYL SULFONES

CROSS-REFERENCE TO RELATED APPLICATION

This application claims the benefit of copending U.S. Provisional Application Serial No. 60/271,990, filed Feb. 28, 2001, the entire disclosure of which is herein incorporated by reference.

FIELD OF THE INVENTION

The invention relates to the field of protecting normal cells and tissues from anticipated, planned or inadvertent exposure to ionizing radiation. In particular, the invention relates to radioprotective agents administered to a subject prior to or after exposure to ionizing radiation, such as occurs during anticancer radiotherapy.

BACKGROUND OF THE INVENTION

Ionizing radiation has an adverse effect on cells and tissues, primarily through cytotoxic effects. In humans, exposure to ionizing radiation occurs primarily through therapeutic techniques (such as anticancer radiotherapy) or through occupational and environmental exposure.

A major source of exposure to ionizing radiation is the administration of therapeutic radiation in the treatment of cancer or other proliferative disorders. Subjects exposed to therapeutic doses of ionizing radiation typically receive between 0.1 and 2 Gy per treatment, and can receive as high as 5 Gy per treatment. Depending on the course of treatment prescribed by the treating physician, multiple doses may be received by a subject over the course of several weeks to several months.

Therapeutic radiation is generally applied to a defined area of the subject's body which contains abnormal proliferative tissue, in order to maximize the dose absorbed by the abnormal tissue and minimize the dose absorbed by the nearby normal tissue. However, it is difficult (if not impossible) to selectively administer therapeutic ionizing radiation to the abnormal tissue. Thus, normal tissue proximate to the abnormal tissue is also exposed to potentially damaging doses of ionizing radiation throughout the course of treatment. There are also some treatments that require exposure of the subject's entire body to the radiation, in a procedure called "total body irradiation", or "TBI." The efficacy of radiotherapeutic techniques in destroying abnormal proliferative cells is therefore balanced by associated cytotoxic effects on nearby normal cells. Because of this, radiotherapy techniques have an inherently narrow therapeutic index which results in the inadequate treatment of most tumors. Even the best radiotherapeutic techniques may result in incomplete tumor reduction, tumor recurrence, increasing tumor burden, and induction of radiation resistant tumors.

Numerous methods have been designed to reduce normal tissue damage while still delivering effective therapeutic doses of ionizing radiation. These techniques include brachytherapy, fractionated and hyperfractionated dosing, complicated dose scheduling and delivery systems, and high voltage therapy with a linear accelerator. However, such techniques only attempt to strike a balance between the therapeutic and undesirable effects of the radiation, and full efficacy has not been achieved.

For example, one treatment for subjects with metastatic tumors involves harvesting their hematopoietic stem cells and then treating the subject with high doses of ionizing radiation. This treatment is designed to destroy the subject's tumor cells, but has the side effect of also destroying their normal hematopoietic cells. Thus, a portion of the subject's bone marrow (containing the hematopoietic stem cells), is removed prior to radiation therapy. Once the subject has been treated, the autologous hematopoietic stem cells are returned to their body.

However, if tumor cells have metastasized away from the tumor's primary site, there is a high probability that some tumor cells will contaminate the harvested hematopoietic cell population. The harvested hematopoietic cell population may also contain neoplastic cells if the subject suffers from a cancers of the bone marrow such as the various French-American-British (FAB) subtypes of acute myelogenous leukemias (AML), chronic myeloid leukemia (CML), or acute lymphocytic leukemia (ALL). Thus, the metastasized tumor cells or resident neoplastic cells must be removed or killed prior to reintroducing the stem cells to the subject. If any living tumorigenic or neoplastic cells are re-introduced into the subject, they can lead to a relapse.

Prior art methods of removing tumorigenic or neoplastic cells from harvested bone marrow are based on a whole-population tumor cell separation or killing strategy, which typically does not kill or remove all of the contaminating malignant cells. Such methods include leukopheresis of mobilized peripheral blood cells, immunoaffinity-based selection or killing of tumor cells, or the use of cytotoxic or photosensitizing agents to selectively kill tumor cells. In the best case, the malignant cell burden may still be at 1 to 10 tumor cells for every 100,000 cells present in the initial harvest (Lazarus et al., *J. Hematotherapy*, 2(4):457–66, 1993).

Thus, there is needed a purging method designed to selectively destroy the malignant cells present in the bone marrow, while preserving the normal hematopoietic stem cells needed for hematopoietic reconstitution in the transplantation subject.

Exposure to ionizing radiation can also occur in the occupational setting. Occupational doses of ionizing radiation may be received by persons who job involves exposure (or potential exposure) to radiation, for example in the nuclear power and nuclear weapons industries. There are currently 104 nuclear power plants licensed for commercial operation in the United States. Internationally, a total of 430 nuclear power plants are operating in 32 countries. All personnel employed in these nuclear power plants may be exposed to ionizing radiation in the course of their assigned duties. Incidents such as the Mar. 28, 1979 accident at Three Mile Island nuclear power plant, which released radioactive material into the reactor containment building and surrounding environment, illustrate the potential for harmful exposure. Even in the absence of catastrophic events, workers in the nuclear power industry are subject to higher levels of radiation than the general public.

Military personnel stationed on vessels powered by nuclear reactors, or soldiers required to operate in areas contaminated by radioactive fallout, risk similar exposure to ionizing radiation. Occupational exposure may also occur in rescue and emergency personnel called in to deal with catastrophic events involving a nuclear reactor or radioactive material. For example, the men who fought the Apr. 26, 1986 reactor fire at the Chernobyl nuclear power plant suffered radiation exposure, and many died from the radiation effects. In August 2000, navy and civilian rescue personnel risked exposure to radiation when attempting to rescue the crew of the downed Russian nuclear-powered submarine Kursk. Salvage crews may still face radiation exposure if the submarine's reactor plant was damaged.

Other sources of occupational exposure may be from machine parts, plastics, and solvents left over from the manufacture of radioactive medical products, smoke alarms, emergency signs, and other consumer goods. Occupational exposure may also occur in persons who serve on nuclear powered vessels, particularly those who tend the nuclear reactors, in military personnel operating in areas contaminated by nuclear weapons fallout, and in emergency personnel who deal with nuclear accidents.

Humans and other animals (such as livestock) may also be exposed to ionizing radiation from the environment. The primary source of exposure to significant amounts of environmental radiation is from nuclear power plant accidents, such as those at Three Mile Island, Chernobyl and Tokaimura. A 1982 study by Sandia National Laboratories estimated that a "worst-case" nuclear accident could result in a death toll of more than 100,000 and long-term radioactive contamination of large areas of land.

For example, the estimated number of deaths from the Chernobyl accident is from 8,000 to 300,000, and in the Ukraine alone, over 4.6 million hectares of land was contaminated with varying levels of radiation. Fallout was detected as far away as Ireland, northern Scandinavia, and coastal Alaska in the first weeks after the accident. 135,000 people were evacuated from a 30-mile radius "dead zone" around the Chernobyl plant, an area which is still not fit for human habitation. Approximately 1.2 million people continue to live in areas of low-level radiation outside the "dead-zone."

Other nuclear power plant accidents have released significant amounts of radiation into the environment. The Three Mile Island accident was discussed above. In Japan, a cracked pipe leaked 51 tons of coolant water from the Tsuruga 2 nuclear plant in July of 1999. A more serious accident occurred on Sep. 30, 1999 at a uranium reprocessing facility in Tokaimura, Japan, where 69 people received significant radiation exposure. The accident occurred when workers inadvertently started a self-sustaining nuclear chain reaction, causing a release of radiation into the atmosphere. A radiation count of 0.84 mSv/hour (4000 times the annual limit) was detected in the immediate area. Thirty-nine households (150 people) were evacuated and 200 meter radius around the site was declared off-limits. The roads within a 3 kilometer radius of the site were closed and residents within 10 kilometer radius of the site were advised to stay indoors. The Tokaimura "criticality event" is ranked as the third most serious accident—behind Three Mile Island and Chernobyl—in the history of the nuclear power industry.

Environmental exposure to ionizing radiation may also result from nuclear weapons detonations (either experimental or during wartime), discharges of actinides from nuclear waste storage and processing and reprocessing of nuclear fuel, and from naturally occurring radioactive materials such as radon gas or uranium. There is also increasing concern that the use of ordnance containing depleted uranium results in low-level radioactive contamination of combat areas.

Radiation exposure from any source can be classified as acute (a single large exposure) or chronic (a series of small low-level, or continuous low-level exposures spread over time). Radiation sickness generally results from an acute exposure of a sufficient dose, and presents with a characteristic set of symptoms that appear in an orderly fashion, including hair loss, weakness, vomiting, diarrhea, skin burns and bleeding from the gastrointestinal tract and mucous membranes. Genetic defects, sterility and cancers (particularly bone marrow cancer) often develop over time. Chronic exposure is usually associated with delayed medical problems such as cancer and premature aging. An acute a total body exposure of 125,000 millirem may cause radiation sickness. Localized doses such as are used in radiotherapy may not cause radiation sickness, but may result in the damage or death of exposed normal cells.

For example, an acute total body radiation dose of 100,000–125,000 millirem (equivalent to 1 Gy) received in less than one week would result in observable physiologic effects such as skin burns or rashes, mucosal and GI bleeding, nausea, diarrhea and/or excessive fatigue. Longer term cytotoxic and genetic effects such as hematopoietic and immunocompetent cell destruction, hair loss (alopecia), gastrointestinal, and oral mucosal sloughing, venoocclusive disease of the liver and chronic vascular hyperplasia of cerebral vessels, cataracts, pneumonites, skin changes, and an increased incidence of cancer may also manifest over time. Acute doses of less than 10,000 millirem (equivalent to 0.1 Gy) typically will not result in immediately observable biologic or physiologic effects, although long term cytotoxic or genetic effects may occur.

A sufficiently large acute dose of ionizing radiation, for example 500,000 to over 1 million millirem (equivalent to 5–10 Gy), may kill a subject immediately. Doses in the hundreds of thousands of millirems may kill within 7 to 21 days from a condition called "acute radiation poisoning." Reportedly, some of the Chernobyl firefighters died of acute radiation poisoning, having received acute doses in the range of 200,000–600,000 millirem (equivalent to 2–6 Gy). Acute doses below approximately 200,000 millirem do not result in death, but the exposed subject will likely suffer long-term cytotoxic or genetic effects as discussed above.

Acute occupational exposures usually occur in nuclear power plant workers exposed to accidental releases of radiation, or in fire and rescue personnel who respond to catastrophic events involving nuclear reactors or other sources of radioactive material. Suggested limits for acute occupational exposures in emergency situations were developed by the Brookhaven National Laboratories, and are given in Table 1.

TABLE 1

Acute Occupational Exposure Limits for Emergency Operations

| Whole Body Conditions for Dose Limit | Activity Required | Conditions for Exposure |
|---|---|---|
| 10,000 millirem* | Protect property | Voluntary, when lower dose not practical |
| 25,000 millirem | Lifesaving Operation; Protect General Public | Voluntary, when lower dose not practical |
| >25,000 millirem | Lifesaving operation; Protect large population | Voluntary, when lower dose not practical, and the risk has been clearly explained |

*100,000 millirem equals one sievert (Sv). For penetrating radiation such as gamma radiation, one Sv equals approximately one Gray (Gy). Thus, the dosage in Gy can be estimated as 1 Gy for every 100,000 millirem.

A chronic dose is a low level (i.e., 100–5000 millirem) incremental or continuous radiation dose received over time. Examples of chronic doses include a whole body dose of ~5000 millirem per year, which is the dose typically received by an adult working at a nuclear power plant. By contrast, the Atomic Energy Commission recommends that members of the general public should not receive more than 100 millirem per year. Chronic doses may cause long-term cytotoxic and genetic effects, for example manifesting as an increased risk of a radiation-induced cancer developing later in life. Recommended limits for chronic exposure to ionizing radiation are given in Table 2.

TABLE 2

Annual Chronic Occupational Radiation Exposure Limits

| Organ or Subject | Annual Occupational Dose in millirem |
|---|---|
| Whole Body | 5000 |
| Lens of the Eye | 15,000 |
| Hands and wrists | 50,000 |
| Any individual organ | 50,000 |
| Pregnant worker | 500/9 months |
| Minor (16–18) receiving training | 100 |

By way of comparison, Table 3 sets forth the radiation doses from common sources.

TABLE 3

Radiation Dosages From Common Sources

| Sources | Dose In Millirem |
|---|---|
| Television | <1/yr |
| Gamma Rays, Jet Cross Country | 1 |
| Mountain Vacation - 2 week | 3 |
| Atomic Test Fallout | 5 |
| U.S. Water, Food & Air (Average) | 30/yr |
| Wood | 50/yr |
| Concrete | 50/yr |
| Brick | 75/yr |
| Chest X-Ray | 100 |
| Cosmic Radiation (Sea Level) | 40/yr (add 1 millirem/100 ft elev.) |
| Natural Background San Francisco | 120/yr |
| Natural Background Denver | 50/yr |
| Atomic Energy Commission Limit For Workers | 5000/yr |
| Complete Dental X-Ray | 5000 |
| Natural Background at Pocos de Caldras, Brazil | 7000/yr |
| Whole Body Diagnostic X-Ray | 100,000 |
| Cancer Therapy | 500,000 (localized) |
| Radiation Sickness-Nagasaki | 125,000 (single doses) |
| LD$_{50}$ Nagasaki & Hiroshima | 400,000–500,000 (single dose) |

Chronic doses of greater than 5000 millirem per year (0.05 Gy per year) may result in long-term cytotoxic or genetic effects similar to those described for persons receiving acute doses. Some adverse cytotoxic or genetic effects may also occur at chronic doses of significantly less than 5000 millirem per year. For radiation protection purposes, it is assumed that any dose above zero can increase the risk of radiation-induced cancer (i.e., that there is no threshold). Epidemiologic studies have found that the estimated lifetime risk of dying from cancer is greater by about 0.04% per rem of radiation dose to the whole body.

While anti-radiation suits or other protective gear may be effective at reducing radiation exposure, such gear is expensive, unwieldy, and generally not available to public. Moreover, radioprotective gear will not protect normal tissue adjacent a tumor from stray radiation exposure during radiotherapy. What is needed, therefore, is a practical way to protect subjects who are scheduled to incur, or are at risk for incurring, exposure to ionizing radiation. In the context of therapeutic irradiation, it is desirable to enhance protection of normal cells while causing tumor cells to remain vulnerable to the detrimental effects of the radiation. Furthermore, it is desirable to provide systemic protection from anticipated or inadvertent total body irradiation, such as may occur with occupational or environmental exposures, or with certain therapeutic techniques.

Pharmaceutical radioprotectants offer a cost-efficient, effective and easily available alternative to radioprotective gear. However, previous attempts at radioprotection of normal cells with pharmaceutical compositions have not been entirely successful. For example, cytokines directed at mobilizing the peripheral blood progenitor cells confer a myeloprotective effect when given prior to radiation (Neta et al., *Semin. Radiat. Oncol.* 6:306–320, 1996), but do not confer systemic protection. Other chemical radioprotectors administered alone or in combination with biologic response modifiers have shown minor protective effects in mice, but application of these compounds to large mammals was less successful, and it was questioned whether chemical radioprotection was of any value (Maisin, J. R., Bacq and Alexander Award Lecture. "Chemical radioprotection: past, present, and future prospects", *Int J. Radiat Biol.* 73:443–50, 1998). Pharmaceutical radiation sensitizers, which are known to preferentially enhance the effects of radiation in cancerous tissues, are clearly unsuited for the general systemic protection of normal tissues from exposure to ionizing radiation.

We have now found that α,β-unsaturated aryl sulfones, in particular benzyl styryl sulfones, provide significant and selective systemic protection of normal cells from radiation-induced damage in animals. When used in radiotherapy techniques, these compounds also show independent toxicity to cancer cells.

SUMMARY OF THE INVENTION

It is an object of the invention to provide compositions and methods for protecting the normal cells and tissues from the cytotoxic and genetic effects of exposure to ionizing radiation, in subjects who have incurred or are at risk of incurring exposure to ionizing radiation. The exposure to ionizing radiation may occur in controlled doses during the treatment of cancer and other proliferative disorders, or may occur in uncontrolled doses beyond the norm accepted for the population at large during high risk activities or environmental exposures.

Thus in one aspect, radioprotective α,β unsaturated aryl sulfone compounds and pharmaceutical compositions comprising radioprotective α,β unsaturated aryl sulfone compounds are provided.

In another aspect, a method of treating a subject for cancer or other proliferative disorders is provided, comprising administering to the subject an effective amount of at least one radioprotectant α,β unsaturated aryl sulfone compound prior to administering an effective amount of ionizing radiation, wherein the radioprotective α,β unsaturated aryl sulfone compound induces a temporary radioresistant phenotype in the subject's normal tissue.

In a further aspect, the invention provides a method of safely increasing the dosage of therapeutic ionizing radiation used in the treatment of cancer or other proliferative disorders, comprising administering an effective amount of at least one radioprotective α,β unsaturated aryl sulfone compound prior to administration of the therapeutic ionizing radiation, which radioprotective compound induces a temporary radioresistant phenotype in the subject's normal tissue.

In yet another embodiment, the invention provides a method for purging bone marrow of neoplastic cells (such as leukemic cells) or tumor cells which have metastasized into the bone marrow, comprising harvesting bone marrow cells from an individual afflicted with a proliferative disorder, treating the harvested bone marrow cells with an effective amount of at least one α,β unsaturated arylsulfone, and subjecting the treated bone marrow cells with to an effective amount of ionizing radiation. The harvested cells are then returned to the body of the afflicted individual.

In yet a further aspect, the invention provides a method for treating individuals who have incurred or are at risk for incurring remediable radiation damage from exposure to ionizing radiation. In one embodiment, an effective amount of at least one radioprotective α,β unsaturated aryl sulfone compound is administered to the subject before the subject incurs remediable radiation damage from exposure to ionizing radiation. In another embodiment, an effective amount of at least one radioprotective α,β unsaturated aryl sulfone compound is administered to the subject after the subject incurs remediable radiation damage from exposure to ionizing radiation.

The term "subject" includes human beings and non-human animals and, as used herein, refers to an organism which is scheduled to incur, is at risk of incurring, or has incurred, exposure to ionizing radiation.

As used herein, "ionizing radiation" is radiation of sufficient energy that, when absorbed by cells and tissues, induces formation of reactive oxygen species and DNA damage. This type of radiation includes X-rays, gamma rays, and particle bombardment (e.g., neutron beam, electron beam, protons, mesons and others), and is used for medical testing and treatment, scientific purposes, industrial testing, manufacturing and sterilization, weapons and weapons development, and many other uses. Radiation is typically measured in units of absorbed dose, such as the rad or gray (Gy), or in units of dose equivalence, such as the rem or sievert (Sv). The relationship between these units is given below:

$$\frac{\text{rad and gray } (Gy)}{1 \text{ rad} = 0.01 \ Gy}$$

$$\frac{\text{rem and sievert } (Sv)}{1 \text{ rem} = 0.01 \ Sv}$$

The Sv is the Gy dosage multiplied by a factor that includes tissue damage done. For example, penetrating ionizing radiation (e.g., gamma and beta radiation) have a factor of about 1, so 1 Sv=~1 Gy. Alpha rays have a factor of 20, so 1 Gy of alpha radiation=20 Sv.

By "effective amount of ionizing radiation" is meant an amount of ionizing radiation effective in killing, or in reducing the proliferation, of abnormally proliferating cells in a subject. As used with respect to bone marrow purging, "effective amount of ionizing radiation" means an amount of ionizing radiation effective in killing, or in reducing the proliferation, of malignant cells in a bone marrow sample removed from a subject.

By "acute exposure to ionizing radiation" or "acute dose of ionizing radiation" is meant a dose of ionizing radiation absorbed by a subject in less than 24 hours. The acute dose may be localized, as in radiotherapy techniques, or may be absorbed by the subjects entire body. Acute doses are typically above 10,000 millirem (0.1 Gy), but may be lower.

By "chronic exposure to ionizing radiation" or "chronic dose of ionizing radiation" is meant a dose of ionizing radiation absorbed by a subject over a period greater than 24 hours. The dose may be intermittent or continuous, and may be localized or absorbed by the subject's entire body. Chronic doses are typically less than 10,000 millirem (0.1 Gy), but may be higher.

By "at risk of incurring exposure to ionizing radiation" is meant that a subject may advertantly (such as by scheduled radiotherapy sessions) or inadvertently be exposed to ionizing radiation in the future. Inadvertent exposure includes accidental or unplanned environmental or occupational exposure.

By "effective amount of the radioprotective α,β unsaturated aryl sulfone compound" is meant an amount of compound effective to reduce or eliminate the toxicity associated with radiation in normal cells of the subject, and also to impart a direct cytotoxic effect to abnormally proliferating cells in the subject. As used with respect to bone marrow purging, "effective amount of the radioprotective α,β unsaturated aryl sulfone compound" means an amount of α,β unsaturated aryl sulfone compound effective to reduce or eliminate the toxicity associated with radiation in bone marrow removed from a subject, and also to impart a direct cytotoxic effect to malignant cells in the bone marrow removed from the subject.

By "α,β unsaturated aryl sulfone compound" as used herein is meant a chemical compound containing one or more α,β unsaturated sulfone groups:

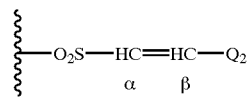

wherein $Q_2$ is substituted or unsubstituted aryl or substituted or unsubstituted heteroaryl, and the hydrogen atoms attached to the α and β carbons are optionally replaced by other chemical groups.

By "substituted" means that an atom or group of atoms has replaced hydrogen as the substituent attached to a ring atom. The degree of substitution in a ring system may be mono-, di-, tri- or higher substitution.

The term "aryl" employed alone or in combination with other terms, means, unless otherwise stated, a carbocyclic aromatic system containing one or more rings (typically one, two or three rings) wherein such rings may be attached together in a pendent manner or may be fused. Examples include phenyl; anthracyl; and naphthyl, particularly 1-naphthyl and 2-naphthyl. The aforementioned listing of aryl moieties is intended to be representative, not limiting. It is understood that the term "aryl" is not limited to ring systems with six members.

The term "heteroaryl" by itself or as part of another substituent means, unless otherwise stated, an unsubstituted or substituted, stable, mono- or multicyclic heterocyclic aromatic ring system which consists of carbon atoms and from one to four heteroatoms selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

Examples of such heteroaryls include benzimidazolyl, particularly 2-benzimidazolyl; benzofuryl, particularly 3-, 4-, 5-, 6- and 7-benzofuryl; 2-benzothiazolyl and 5-benzothiazolyl; benzothienyl, particularly 3-, 4-, 5-, 6-, and 7-benzothienyl; 4-(2-benzyloxazolyl); furyl, particularly 2- and 3-furyl; isoquinolyl, particularly 1- and 5-isoquinolyl; isoxazolyl, particularly 3-, 4- and 5-isoxazolyl; imidazolyl, particularly 2-, -4 and 5-imidazolyl; indolyl, particularly 3-, 4-, 5-, 6- and 7-indolyl; oxazolyl, particularly 2-, 4- and 5-oxazolyl; purinyl; pyrrolyl, particularly 2-pyrrolyl, 3-pyrrolyl; pyrazolyl, particularly 3- and 5-pyrazolyl; pyrazinyl, particularly 2-pyrazinyl; pyridazinyl, particularly 3- and 4-pyridazinyl; pyridyl, particularly 2-, 3- and 4-pyridyl; pyrimidinyl, particularly 2- and 4-pyrimidyl; quinoxalinyl, particularly 2- and 5-quinoxalinyl; quinolinyl, particularly 2- and 3-quinolinyl; 5-tetrazolyl; 2-thiazolyl; particularly 2-thiazolyl, 4-thiazolyl and 5-thiazolyl; thienyl, particularly 2- and 3-thienyl; and 3-(1,2,4-triazolyl). The aforementioned listing of heteroaryl moieties is intended to be representative, not limiting.

According to one embodiment, the α,β unsaturated aryl sulfone group is a styryl sulfone group:

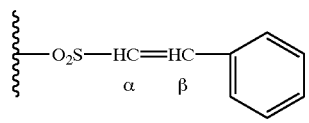

wherein the hydrogen atoms attached to the α and β carbons are optionally replaced by other chemical groups, and the phenyl ring is optionally substituted.

By "styryl sulfone" or "styryl sulfone compound" or "styryl sulfone therapeutic" as used herein is meant a chemical compound containing one or more such styryl sulfone groups.

The α,β unsaturated aryl sulfone radioprotective compounds are characterized by cis-trans isomerism resulting from the presence of a double bond. Stearic relations around a double bond are designated as "Z" or "E". Both configurations are included in the scope of "α,β unsaturated aryl sulfone":

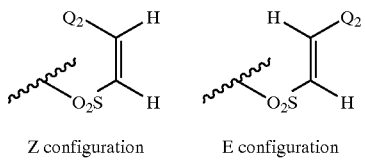

Z configuration      E configuration

According to one embodiment, the α,β unsaturated aryl sulfone compound is a compound of the formula I:

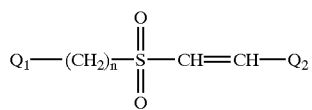

I wherein:
n is one or zero;
$Q_1$ and $Q_2$ are, same or different, are substituted or unsubstituted aryl, or substituted or unsubstituted heteroaryl.

Preferably, n in formula I is one, that is, the compounds comprise α,β unsaturated benzylsulfones, e.g. styryl benzylsulfones.

In one preferred embodiment according to formula I, $Q_1$ and/or $Q_2$ are selected from substituted and unsubstituted heteroaryl; for example, (E)-3-furanethenyl-2,4-dichlorobenzylsulfone.

In another preferred embodiment according to formula 1, $Q_1$ and $Q_2$ are selected from substituted and unsubstituted phenyl.

Preferred compounds where $Q_1$ and $Q_2$ are selected from substituted and unsubstituted phenyl comprise compounds of the formula II:

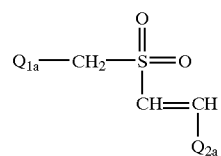

II wherein:
$Q_{1a}$ and $Q_{2a}$ are independently selected from the group consisting of phenyl and mono-, di-, tri-, tetra- and penta-substituted phenyl where the substituents, which may be the same or different, are independently selected from the group consisting of hydrogen, halogen, C1–C8 alkyl, C1–C8 alkoxy, nitro, cyano, carboxy, hydroxy, phosphonato, amino, sulfamyl, acetoxy, dimethylamino(C2–C6 alkoxy), C1–C6 trifluoroalkoxy and trifluoromethyl.

In one embodiment, compounds of formula II are at least di-substituted on at least one ring, that is, at least two substituents on at least one ring are other than hydrogen. In another embodiment, compounds of formula II are at least trisubstituted on at least one ring, that is, at least three substituents on at least one ring are other than hydrogen.

In one embodiment, the radioprotective compound has the formula III:

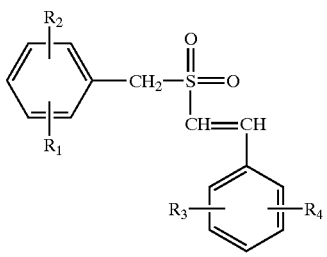

(III)

wherein $R_1$, $R_2$, $R_3$ and $R_4$ are independently selected from the group consisting of hydrogen, halogen, C1–C8 alkyl, C1–C8 alkoxy, nitro, cyano, carboxy, hydroxy phosphonato, amino, sulfamyl, acetoxy, dimethylamino(C2–C6 alkoxy), C1–C6 trifluoroalkoxy and trifluoromethyl.

According to a particularly preferred embodiment of the invention, the radioprotective compound is according to formula III, and $R_1$ and $R_2$ are independently selected from the group consisting of hydrogen, halogen, cyano, and trifluoromethyl; and $R_3$ and $R_4$ are independently selected from the group consisting of hydrogen and halogen.

According to one sub-embodiment of formula III, the radioprotective α,β unsaturated aryl sulfone compound is a compound of the formula IIIa, wherein $R_2$ and $R_4$ are other than hydrogen:

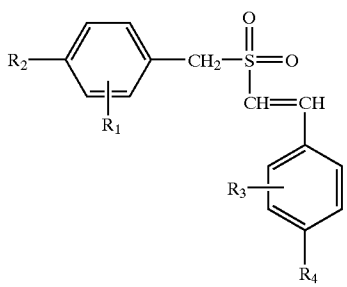

IIIa

Preferred compounds according to formula IIIa having the E-configuration include, but are not limited to, (E)-4-fluorostyryl-4-chlorobenzylsulfone; (E)-4-chlorostyryl-4-chlorobenzylsulfone; (E)-2-chloro-4-fluorostyryl-4-chlorobenzylsulfone; (E)-4-carboxystyryl-4-chlorobenzyl sulfone; (E)-4-fluorostyryl-2,4-dichlorobenzylsulfone; (E)-4-fluorostyryl-4-bromobenzylsulfone; (E)-4-chlorostyryl-4-bromobenzylsulfone; (E)-4-bromostyryl-4-chlorobenzylsulfone; (E)-4-fluorostyryl-4-trifluoromethylbenzylsulfone; (E)-4-fluorostyryl-3,4-dichlorobenzylsulfone; (E)-4-fluorostyryl-4-cyanobenzylsulfone; (E)-2,4-dichloro-4-chlorobenzylsulfone; (E)-4-fluorostyryl-4-chlorophenylsulfone and (E)-4-chlorostyryl-2,4-dichlorobenzylsulfone.

According to another embodiment, compounds of formula IIIa have the Z configuration wherein $R_1$ and $R_3$ are hydrogen, and $R_2$ and $R_4$ are selected from the group consisting of 4-halogen. Such compounds include, for example, (Z)-4-chlorostyryl-4-chlorobenzylsulfone; (Z)-4-chlorostyryl-4-fluorobenzylsulfone; (Z)-4-fluorostyryl-4-chlorobenzylsulfone; (Z)-4-bromostyryl-4-chlorobenzylsulfone; and (Z)-4-bromostyryl-4-fluorobenzylsulfone.

According to another embodiment, the radioprotective α,β unsaturated aryl sulfone compound is a compound of the formula IV:

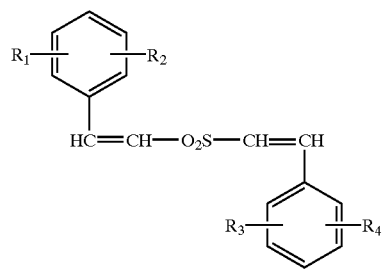

IV wherein $R_1$, $R_2$, $R_3$, and $R_4$ are independently selected from the group consisting of hydrogen, halogen, C1–8 alkyl, C1–8 alkoxy, nitro, cyano, carboxy, hydroxy, and trifluoromethyl.

In one embodiment, $R_1$ in formula IV is selected from the group consisting of hydrogen, chlorine, fluorine and bromine; and $R_2$, $R_3$ and $R_4$ are hydrogen. A preferred compound of formula IV is (Z)-styryl-(E)-2-methoxy-4-ethoxystyrylsulfone.

According to yet another embodiment, the radioprotective α,β unsaturated aryl sulfone compound is a compound of the formula V:

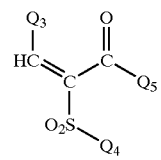

V wherein $Q_3$, $Q_4$ and $Q_5$ are independently selected from the group consisting of phenyl and mono-, di-, tri-, tetra- and penta-substituted phenyl where the substituents, which may be the same or different, are independently selected from the group consisting of halogen, C1–C8 alkyl, C1–C8 alkoxy, nitro, cyano, carboxy, hydroxy, phosphonato, amino, sulfamyl, acetoxy, dimethylamino(C2–C6 alkoxy), C1–C6 trifluoroalkoxy and trifluoromethyl.

According to one sub-embodiment of formula V, the radioprotective α,β unsaturated aryl sulfone compound is a compound of the formula Va:

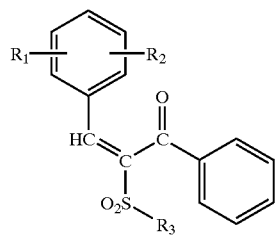

Va wherein
- R₁ and R₂ are independently selected from the group consisting of hydrogen, halogen, C1–C8 alkyl, C1–8 alkoxy, nitro, cyano, carboxyl, hydroxyl, and trifluoromethyl; and
- R₃ is selected from the group consisting of unsubstituted phenyl, mono-substituted phenyl and di-substituted phenyl, the substituents on the phenyl ring being independently selected from the group consisting of halogen and C1–8 alkyl.

Preferably, R₁ in formula Va is selected from the group consisting of fluorine and bromine; R₂ is hydrogen; and R₃ is selected from the group consisting of 2-chlorophenyl, 4-chlorophenyl, 4-fluorophenyl, and 2-nitrophenyl.

A preferred radioprotective styryl sulfone according to formula Va is the compound wherein R₁ is fluorine, R₂ is hydrogen and R₃ is phenyl, that is, the compound 2-(phenylsulfonyl)-1-phenyl-3-(4-fluorophenyl)-2-propen-1-one.

By "dimethylamino(C2–C6 alkoxy)" is meant (CH₃)₂N(CH₂)ₙO— wherein n is from 2 to 6. Preferably, n is 2 or 3. Most preferably, n is 2, that is, the group is the dimethylaminoethoxy group, that is, (CH₃)₂NCH₂CH₂O—.

By "phosphonato" is meant the group —PO(OH)₂.

By "sulfamyl" is meant the group —SO₂NH₂.

Where a substituent on an aryl nucleus is an alkoxy group, the carbon chain may be branched or straight, with straight being preferred. Preferably, the alkoxy groups comprise C1–C6 alkoxy, more preferably C1–C4 alkoxy, most preferably methoxy.

DETAILED DESCRIPTION OF THE INVENTION

Figure 1A:
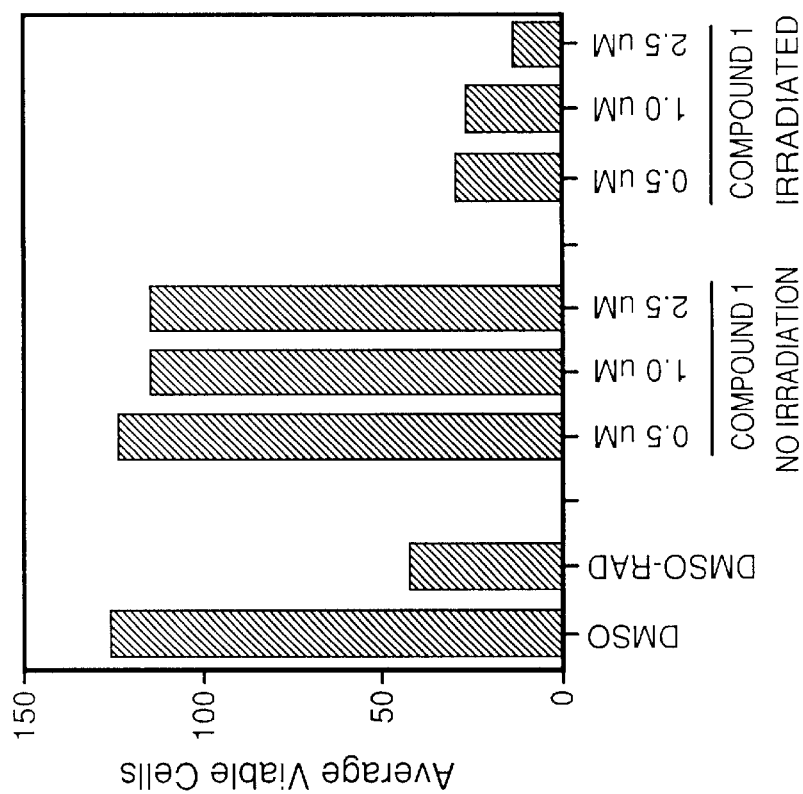
FIGS. 1A and 1B show the effect of 5 Gy and 10 Gy of ionizing radiation, respectively, on the viability of DU145 prostate tumor cells in the presence or absence of (E)-4-fluorostyryl-4-chlorobenzylsulfone.
Figure 1B:
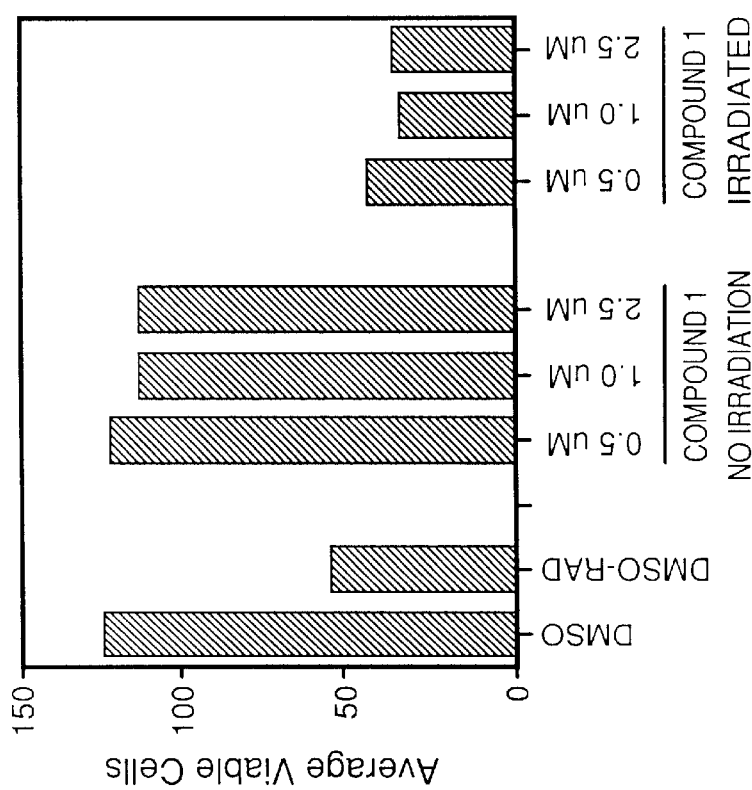
Figure 2A:
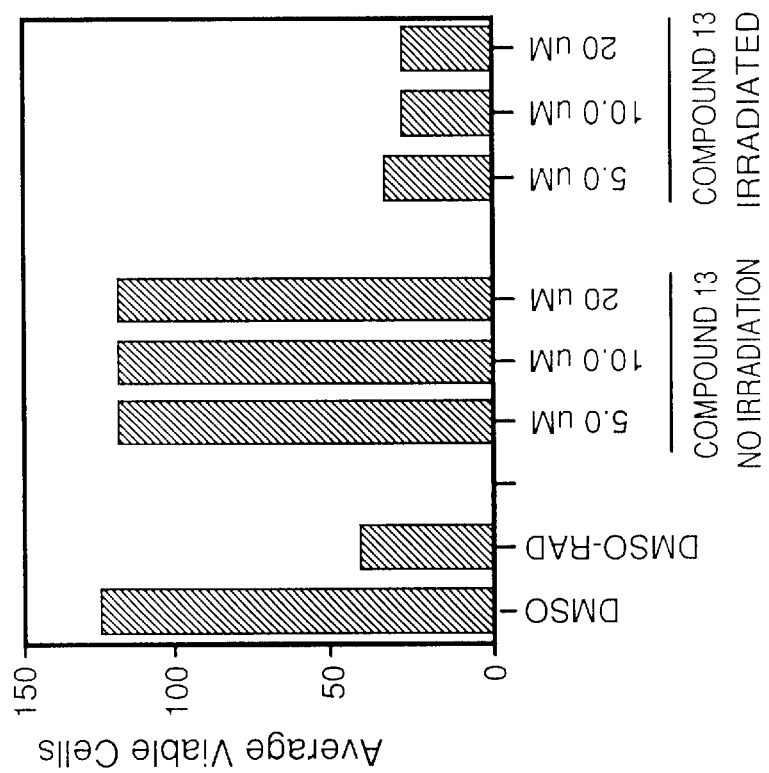
FIGS. 2A and 2B show the effect of 5 Gy and 10 Gy of ionizing radiation, respectively, on the viability of DU145 prostate tumor cells in the presence or absence of (E)-4-carboxystyryl-4-chlorobenzylsulfone.
Figure 2B:
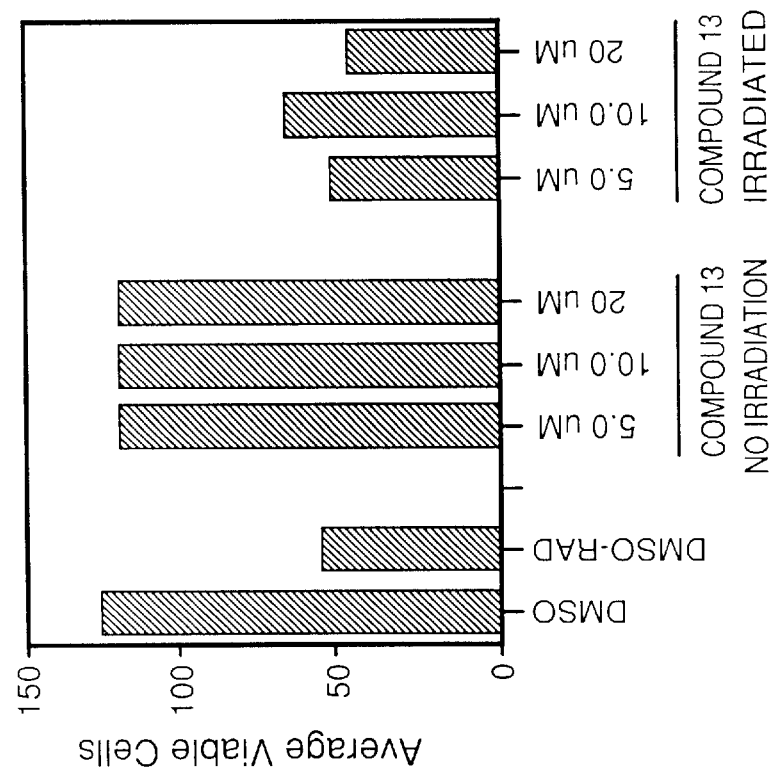

The α,β unsaturated aryl sulfones of the invention protect normal cells and tissues from the effects of acute and chronic exposure to ionizing radiation.

Some of these α,β unsaturated aryl sulfones are also operationally cytotoxic in tumor cells. Data indicating the cytotoxic effect of α,β unsaturated aryl sulfone compounds on tumor cells is set forth in PCT/US/98/20580, PCT/US00/08350 and PCTUS00/08565, the entire disclosures of which are incorporated herein by reference.

The precise radioprotectant mechanism of action of the α,β unsaturated aryl sulfones on normal cells is unknown. However, based on experimental models, and without wishing to be bound by any theory, these compounds may affect several elements in normal cells which induce a reversible quiescent cell-cycling state in which transit through mitosis, and many of the changes necessary for such passage, are down regulated, inactivated or absent. According to other possible mechanisms of protection, radiation-induced reactive oxygen molecules, DNA damage, and activation of death-pathway induction may be rendered innocuous by pre-exposure to α,β unsaturated aryl sulfones.

The mechanisms of radioprotection induced by α,β unsaturated aryl sulfones are different from the mechanism of chemoprotection induced by α,β unsaturated aryl sulfone species which protect normal cells from acute death from mitotic phase cell cycle inhibitors such as the taxoids and vinca alkaloids.

Mitotic phase cell cycle inhibitors affect cells differently than ionizing radiation. For example, the mitotic phase cell cycle inhibitors do not cause cell death by DNA damage, and do not allow the cell to proceed past the GI phase. Ionizing radiation damages DNA and causes cell cycle arrest in the G2 phase. Also, cells exposed to mitotic phase cell cycle inhibitors do not exhibit damage in the long term, but show only acute effects. By contrast, some effects from ionizing radiation may not be evident until at least two weeks after exposure, with damage to bone marrow appearing after 30 days, and neurologic damage manifesting up to six months after exposure. Furthermore, α,β unsaturated aryl sulfones do not provide a chemoprotective effect against "radiomimetic" drugs. Radiomimetic drugs are compounds that induce DNA damage and/or generation of oxygen radicals in the cell, analogous to ionizing radiation.

Subjects may be exposed to ionizing radiation when undergoing therapeutic irradiation for the treatment of proliferative disorders. Such disorders included cancerous and non-cancer proliferative disorders. For example, the present compounds are believed effective in protecting normal cells during therapeutic irradiation of a broad range of tumor types, including but not limited to the following: breast, prostate, ovarian, lung, colorectal, brain (i.e., glioma) and renal. The compounds are also effective against leukemic cells.

The compounds are also believed useful in protecting normal cells during therapeutic irradiation of abnormal tissues in non-cancer proliferative disorders, including but not limited to the following: hemangiomatosis in new born, secondary progressive multiple sclerosis, chronic progressive myelodegenerative disease, neurofibromatosis, ganglioneuromatosis, keloid formation, Paget's Disease of the bone, fibrocystic disease of the breast, Peronies and Duputren's fibrosis, restenosis and cirrhosis.

According to the invention, therapeutic ionizing radiation may be administered to a subject on any schedule and in any dose consistent with the prescribed course of treatment, as long as the α,β unsaturated aryl sulfone radioprotectant compound is administered prior to the radiation. The course of treatment differs from subject to subject, and those of ordinary skill in the art can readily determine the appropriate dose and schedule of therapeutic radiation in a given clinical situation.

The α,β unsaturated aryl sulfone should be administered far enough in advance of the therapeutic radiation such that the compound is able to reach the normal cells of the subject in sufficient concentration to exert a radioprotective effect on the normal cells. The α,β unsaturated aryl sulfone may be administered as much as about 24 hours, preferably no more than about 18 hours, prior to administration of the radiation. In one embodiment, the α,β unsaturated aryl sulfone is administered at least about 6–12 hours before administration of the therapeutic radiation. Most preferably, the α,β unsaturated aryl sulfone is administered once at about 18 hours and again at about 6 hours before the radiation exposure. One or more α,β unsaturated aryl sulfones may be administered simultaneously, or different α,β unsaturated aryl sulfones may be administered at different times during the treatment.

Where the therapeutic radiation is administered in serial fashion, it is preferable to intercalate administration of one or more α,β unsaturated aryl sulfones within the schedule of radiation treatments. As above, different α,β unsaturated aryl sulfones may be administered either simultaneously or at different times during the treatment. Preferably, an about 24 hour period separates administration of α,β unsaturated aryl sulfone and the therapeutic radiation. More preferably, the administration of α,β unsaturated aryl sulfone and the therapeutic radiation is separated by about 6 to 18 hours. This strategy will yield significant reduction in radiation-induced side effects without affecting the anticancer activity of the therapeutic radiation.

For example, therapeutic radiation at a dose of 0.1 Gy may be given daily for five consecutive days, with a two day rest, for a total period of 6–8 weeks. One or more α,β unsaturated aryl sulfones may be administered to the subject 18 hours previous to each round of radiation. It should be pointed out, however, that more aggressive treatment schedules, i e., delivery of a higher dosage, is contemplated according to the present invention due to the protection of the normal cells afforded by the α,β unsaturated aryl sulfones. Thus, the radioprotective effect of the α,β unsaturated aryl sulfone increases the therapeutic index of the therapeutic radiation, and may permit the physician to safely increase the dosage of therapeutic radiation above presently recommended levels without risking increased damage to the surrounding normal cells and tissues.

The α,β unsaturated arylsulfone of the invention are further useful in protecting normal bone marrow cells from radiologic treatments designed to destroy hematologic neoplastic cells or tumor cells which have metastasized into the bone marrow. Such cells include, for example, myeloid leukemia cells. The appearance of these cells in the bone marrow and elsewhere in the body is associated with various disease conditions, such as the French-American-British (FAB) subtypes of acute myelogenous leukemias (AML), chronic myeloid leukemia (CML), and acute lymphocytic leukemia (ALL). CML, in particular, is characterized by abnormal proliferation of immature granulocytes (e.g., neutrophils, eosinophils, and basophils) in the blood, bone marrow, spleen, liver, and other tissues and accumulation of granulocytic precursors in these tissues. The subject who presents with such symptoms will typically have more than 20,000 white blood cells per microliter of blood, and the count may exceed 400,000. Virtually all CML patients will develop "blast crisis", the terminal stage of the disease during which immature blast cells rapidly proliferate, leading to death.

Other subjects suffer from metastatic tumors, and require treatment with total body irradiation (TBI). Because TBI will also kill the subject's hematopoietic cells, a portion of the subject's bone marrow is removed prior to irradiation for subsequent reimplantation. However, metastatic tumor cells are likely present in the bone marrow, and reimplantation often results in a relapse of the cancer within a short time.

Subjects presenting with neoplastic diseases of the bone marrow or metastatic tumors may be treated by removing a portion of the bone marrow (also called "harvesting"), purging the harvested bone marrow of malignant stem cells, and reimplanting the purged bone marrow. Preferably, the subject is simultaneously treated with radiation or some other anti-cancer therapy.

Thus, the invention provides a method of reducing the number of malignant cells in bone marrow, comprising the steps of removing a portion of the subject's bone marrow, administering an effective amount of at least one α,β unsaturated arylsulfone and irradiating the treated bone marrow with a sufficient dose of ionizing radiation such that neoplastic or tumor cells in the bone marrow are killed. As used herein, "malignant cell" means any uncontrollably proliferating cell, such a tumor cell or neoplastic cell. The α,β unsaturated aryl sulfone protects the normal hematopoietic cells present in the bone marrow from the deleterious effects of the ionizing radiation. The α,β unsaturated arylsulfone also exhibits a direct killing effect on the malignant cells. The number of malignant cells in the bone marrow is significantly reduced prior to reimplantation, thus minimizing the occurrence of a relapse.

Preferably, each α,β unsaturated arylsulfone is administered in a concentration from about 0.25 to about 100 micromolar; more preferably, from about 1.0 to about 50 micromolar; in particular from about 2.0 to about 25 micromolar. Particularly preferred concentrations are 0.5, 1.0 and 2.5 micromolar and 5, 10 and 20 micromolar. Higher or lower concentrations may also be used.

The α,β unsaturated arylsulfones may be added directly to the harvested bone marrow, but are preferably dissolved in an organic solvent such as dimethylsulfoxide (DMSO). Pharmaceutical formulations of α,β unsaturated arylsulfones such as are described in more detail below may also be used.

Preferably, the α,β unsaturated arylsulfone is added to the harvested bone marrow about 20 hours prior to radiation exposure, preferably no more than about 24 hours prior to radiation exposure. In one embodiment, the α,β unsaturated aryl sulfone is administered to the harvested bone marrow at least about 6 hours before radiation exposure. One or more α,β unsaturated aryl sulfones may be administered simultaneously, or different α,β unsaturated aryl sulfones may be administered at different times. Other dosage regimens may also be used.

If the subject is to be treated with ionizing radiation prior to reimplantation of the purged bone marrow, the subject may be treated with one or more α,β unsaturated aryl sulfones prior to receiving the ionizing radiation dose, as described above.

A subject may also be exposed to ionizing radiation from occupation or environmental sources, as discussed in the background section. For purposes of the invention, the source of the radiation is not as important as the type (i.e., acute or chronic) and dose level absorbed by the subject. It is understood that the following discussion encompasses ionizing radiation exposures from both occupational and environmental sources.

Subjects suffering from effects of acute or chronic exposure to ionizing radiation that are not immediately fatal are said to have remediable radiation damage. Such remediable radiation damage can reduced or eliminated by the compounds and methods of the present invention.

An acute dose of ionizing radiation which may cause remediable radiation damage includes a localized or whole body dose, for example, between about 10,000 millirem (0.1 Gy) and about 1,000,000 millirem (10 Gy) in 24 hours or less, preferably between about 25,000 millirem (0.25 Gy) and about 200,000 (2 Gy) in 24 hours or less, and more preferably between about 100,000 millirem (1 Gy) and about 150,000 millirem (1.5 Gy) in 24 hours or less.

A chronic dose of ionizing radiation which may cause remediable radiation damage includes a whole body dose of about 100 millirem (0.001 Gy) to about 10,000 millirem (0.1 Gy), preferably a dose between about 1000 millirem (0.01 Gy) and about 5000 millirem (0.05 Gy) over a period greater than 24 hours, or a localized dose of 15,000 millirem (0.15 Gy) to 50,000 millirem (0.5 Gy) over a period greater than 24 hours.

The invention therefore provides a method for treating individuals who have incurred remediable radiation damage from acute or chronic exposure to ionizing radiation, comprising reducing or eliminating the cytotoxic effects of radiation exposure on normal cells and tissues by administering an effective amount of at least one radioprotective $\alpha,\beta$ unsaturated aryl sulfone compound. The compound is preferably administered in as short a time as possible following radiation exposure, for example between 0–6 hours following exposure.

Remediable radiation damage may take the form of cytotoxic and genotoxic (i.e., adverse genetic) effects in the subject. In another embodiment, there is therefore provided a method of reducing or eliminating the cytotoxic and genotoxic effects of radiation exposure on normal cells and tissues, comprising administering an effective amount of at least one radioprotective $\alpha,\beta$ unsaturated aryl sulfone compound prior to acute or chronic radiation exposure. The $\alpha,\beta$ unsaturated aryl sulfone may be administered, for example about 24 hours prior to radiation exposure, preferably no more than about 18 hours prior to radiation exposure. In one embodiment, the $\alpha,\beta$ unsaturated aryl sulfone is administered at least about 6 hours before radiation exposure. Most preferably, the $\alpha,\beta$ unsaturated aryl sulfone is administered at about 18 and again at about 6 hours before the radiation exposure. One or more $\alpha,\beta$ unsaturated aryl sulfones may be administered simultaneously, or different $\alpha,\beta$ unsaturated aryl sulfones may be administered at different times.

When multiple acute exposures are anticipated, the $\alpha,\beta$ unsaturated aryl sulfones may be administered multiple times. For example, if fire or rescue personnel must enter contaminated areas multiple times, $\alpha,\beta$ unsaturated aryl sulfones may be administered prior to each exposure. Preferably, an about 24 hour period separates administration of $\alpha,\beta$ unsaturated aryl sulfone and the radiation exposure. More preferably, the administration of $\alpha,\beta$ unsaturated aryl sulfone and the radiation exposure is separated by about 6 to 18 hours. It is also contemplated that a worker in a nuclear power plant may be administered an effective amount of $\alpha,\beta$ unsaturated aryl sulfones prior to beginning each shift, to reduce or eliminate the effects of exposure to ionizing radiation.

If a subject is anticipating chronic exposure to ionizing radiation, the $\alpha,\beta$ unsaturated aryl sulfones may be administered periodically throughout the duration of anticipated exposure. For example, a nuclear power plant worker or a soldier operating in a forward area contaminated with radioactive fallout may be given $\alpha,\beta$ unsaturated aryl sulfone every 24 hours, preferably every 6–18 hours, in order to mitigate the effects of radiation damage. Likewise, $\alpha,\beta$ unsaturated aryl sulfones may be periodically administered to civilians living in areas contaminated by radioactive fallout until the area is decontaminated or the civilians are removed to a safer environment.

As used herein, "administered" means the act of making the $\alpha,\beta$ unsaturated aryl sulfone available to the subject such that a pharmacologic effect of radioprotection is realized. This pharmacologic effect may manifest as the absence of expected physiologic or clinical symptoms at a certain level of radiation exposure. One skilled in the art may readily determine the presence or absence of radiation-induced effects, by well-known laboratory and clinical methods. The $\alpha,\beta$ unsaturated aryl sulfone compound may thus be administered by any route which is sufficient to bring about the desired radioprotective effect in the patient. Routes of administration include, for example enteral (e.g., oral, rectal, intranasal, etc.) and parenteral administration. Parenteral administration includes, for example, intravenous, intramuscular, intraarterial, intraperitoneal, intravaginal, intravesical (e.g., into the bladder), intradermal, topical or subcutaneous administration. Also contemplated within the scope of the invention is the instillation of drug in the body of the patient in a controlled formulation, with systemic or local release of the drug to occur at a later time. For example, a depot of $\alpha,\beta$ unsaturated aryl sulfone maybe administered to the patient more than 24 hours before the administration of radiation. Preferably, at least a portion of the $\alpha,\beta$ unsaturated aryl sulfone is retained in the depot and not released until an about 6–18 hour window prior to the radiation exposure.

The $\alpha,\beta$ unsaturated aryl sulfone may be administered in the form of a pharmaceutical composition comprising one or more $\alpha,\beta$ unsaturated aryl sulfones in combination with a pharmaceutically acceptable carrier. The $\alpha,\beta$ unsaturated aryl sulfone in such formulations may comprise from 0.1 to 99.99 weight percent. By "pharmaceutically acceptable carrier" is meant any carrier, diluent or excipient which is compatible with the other ingredients of the formulation and is not deleterious to the subject. It is within the skill in the art to formulate appropriate pharmaceutical compositions with $\alpha,\beta$ unsaturated aryl sulfones.

For example, the $\alpha,\beta$ unsaturated aryl sulfones may be formulated into pharmaceutical compositions according to standard practices in the field of pharmaceutical preparations. See Alphonso Gennaro, ed., Remington's Pharmaceutical Sciences, 18th Ed., (1990) Mack Publishing Co., Easton, Pa. Suitable pharmaceutical compositions include, for example, tablets, capsules, solutions (especially parenteral solutions), troches, suppositories, or suspensions.

For parenteral administration, the $\alpha,\beta$ unsaturated aryl sulfone may be mixed with a suitable carrier or diluent such as water, an oil, saline solution, aqueous dextrose (glucose) and related sugar solutions, cyclodextrans or a glycol such as propylene glycol or polyethylene glycol. Solutions for parenteral administration preferably contain a pharmaceutically acceptable, water soluble salt of the $\alpha,\beta$ unsaturated aryl sulfone. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol.

For oral administration, the α,β unsaturated aryl sulfone may be combined with one or more solid inactive ingredients for the preparation of tablets, capsules, or other suitable oral dosage forms. For example, the active agent may be combined with carboxymethylcellulose calcium, magnesium stearate, mannitol and starch, and then formed into tablets by conventional tableting methods.

The specific dose and schedule of α,β unsaturated aryl sulfone to obtain the radioprotective benefit will, of course, be determined by the particular circumstances of the individual patient including, the size, weight, age and sex of the patient, the nature and stage of the disease being treated, the aggressiveness of the disease, and the route of administration, and the specific toxicity of the radiation. For example, a daily dosage of from about 0.01 to about 150 mg/kg/day may be utilized, more preferably from about 0.05 to about 50 mg/kg/day. Particularly preferred are doses from about 1.0 to about 10.0 mg/kg/day, for example, a dose of about 7.0 mg/kg/day. The dose may be given over multiple administrations, for example, two administrations of 3.5 mg/kg. Higher or lower doses are also contemplated.

The α,β unsaturated aryl sulfones may take the form or pharmaceutically acceptable salts. The term "pharmaceutically acceptable salts" embraces salts commonly used to form alkali metal salts and to form addition salts of free acids or free bases. The nature of the salt is not critical, provided that it is pharmaceutically-acceptable. Suitable pharmaceutically acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, betahydroxybutyric, galactaric and galacturonic acid. Suitable pharmaceutically acceptable base addition salts include metallic salts made from calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding α,β unsaturated aryl sulfone by reacting, for example, the appropriate acid or base with the sulfone compound.

The α,β unsaturated aryl sulfones are characterized by cis-trans isomerism resulting from the presence of one or more double bonds. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4<sup>th</sup> ed., 1992, p. 127–138. Stearic relations around a double bond are designated as "Z" or "E".

(E)-α,β unsaturated aryl sulfones may be prepared by Knoevenagel condensation of aromatic aldehydes with benzylsulfonyl acetic acids or arylsulfonyl acetic acids. The procedure is described by Reddy et al., *Acta. Chim. Hung* 115:269–71 (1984); Reddy et al., *Sulfur Letters* 13:83–90 (1991); Reddy et al., *Synthesis* No. 4, 322–23 (1984); and Reddy et al., *Sulfur Letters* 7:43–48 (1987), the entire disclosures of which are incorporated herein by reference.

According to the Scheme 1 below, $R_a$ and $R_b$ each represent from zero to five substituents on the depicted aromatic nucleus. For purposes of illustration, and not limitation, the aryl groups are represented as phenyl groups, that is, the synthesis is exemplified by the preparation of styryl benzylsulfones. Accordingly, the benzyl thioacetic acid B is formed by the reaction of sodium thioglycollate and a benzyl chloride A. The benzyl thioacetic acid B is then oxidized with 30% hydrogen peroxide to give a corresponding benzylsulfonyl acetic acid C. Condensation of the benzylsulfonyl acetic acid C with an aromatic aldehyde D via a Knoevenagel reaction in the presence of benzylamine and glacial acetic acid yields the desired (E)-styryl benzylsulfone E.

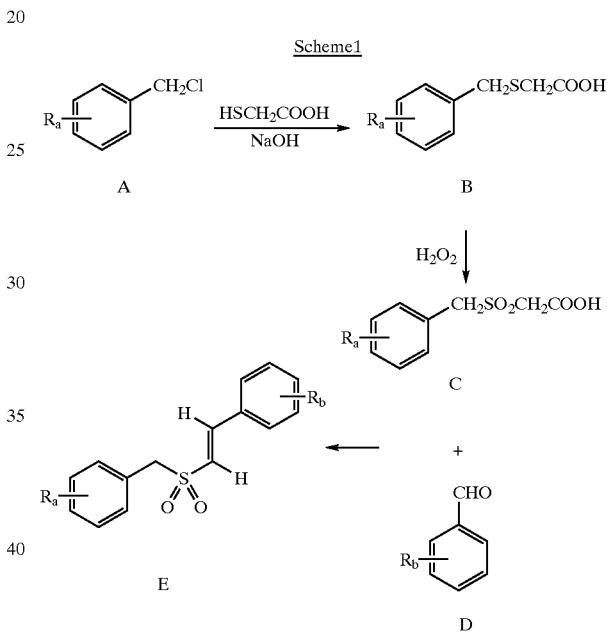

Scheme 1

The following is a more detailed two-part synthesis procedure for preparing (E)-styryl benzylsulfones according to the above scheme.

General Procedure 1: Synthesis (E)-Styryl Benzylsulfones

Part A. To a solution of (8 g, 0.2 mol) sodium hydroxide in methanol (200 ml), thioglycollic acid (0.1 mol) is added slowly and the precipitate formed is dissolved by stirring the contents of the flask. Then an appropriately substituted benzyl chloride (0.1 mol) is added stepwise and the reaction mixture is refluxed for 2–3 hours. The cooled contents are poured onto crushed ice and neutralized with dilute hydrochloric acid (200 ml). The resulting corresponding benzylthioacetic acid (0.1 mol) is subjected to oxidation with 30% hydrogen peroxide (0.12 mol) in glacial acetic acid (125 ml) by refluxing for 1 hour. The contents are cooled and poured onto crushed ice. The separated solid is recrystalized from hot water to give the corresponding pure benzylsulfonylacetic acid.

Part B. A mixture of the benzylsulfonyl acetic acid (10 mmol), an appropriately substituted aromatic aldehyde (10 mmol), and benzylamine (0.2 ml) in glacial acetic acid (12 ml) is refluxed for 2–3 hours. The contents are cooled and treated with cold ether (50 ml). Any product precipitated out is separated by filtration. The filtrate is diluted with more ether and washed successively with a saturated solution of sodium bicarbonate (20 ml), sodium bisulfite (20 ml), dilute hydrochloric acid (20 ml) and finally with water (35 ml). Evaporation of the dried ethereal layer yields styryl benzylsulfones as a solid material.

According to an alternative to Part A, the appropriate benzylsulfonylacetic acids may be generated by substituting a thioglycollate $HSCH_2COOR$ for thioglycollic acid, where R is an alkyl group, typically C1–C6 alkyl. This leads to the formation of the alkylbenzylthioacetate intermediate (F),

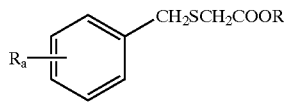

which is then converted to the corresponding benzyl thioacetic acid B by alkaline or acid hydrolysis.

(E)-styryl phenyl sulfones (formula I: n=zero; $Q_1$, $Q_2$=substituted or unsubstituted phenyl) are prepared according to the method of General Procedure 1, replacing the benzylsulfonyl acetic acid in Part B with the appropriate substituted or unsubstituted phenylsulfonyl acetic acid.

(Z)-Styryl benzylsulfones are prepared by the nucleophilic addition of the appropriate thiols to substituted phenylacetylene with subsequent oxidation of the resulting sulfide by hydrogen peroxide to yield the (Z)-styryl benzylsulfone. The procedure is generally described by Reddy et al., *Sulfur Letters* 13:83–90 (1991), the entire disclosure of which is incorporated herein as a reference.

In the first step of the (Z)-styryl benzylsulfones synthesis, the sodium salt of benzyl mercaptan or the appropriate substituted benzyl mercaptan is allowed to react with phenylacetylene or the appropriate substituted phenylacetylene forming the pure (Z)-isomer of the corresponding styryl benzylsulfide in good yield.

In the second step of the synthesis, the (Z)-styryl benzylsulfide intermediate is oxidized to the corresponding sulfone in the pure (Z)-isomeric form by treatment with hydrogen peroxide.

The following is a more detailed two-part synthesis procedure for preparing (Z)-styryl benzylsulfones:

Procedure 2: Synthesis of (Z)-Styryl Benzylsulfones

Part A. To a refluxing methanolic solution of substituted or unsubstituted sodium benzylthiolate prepared from 460 mg (0.02 g atom) of (i) sodium, (ii) substituted or unsubstituted benzyl mercaptan (0.02 mol) and (iii) 80 ml of absolute methanol, is added freshly distilled substituted or unsubstituted phenylacetylene. The mixture is refluxed for 20 hours, cooled and then poured on crushed ice. The crude product is filtered, dried and recrystalized from methanol or aqueous methanol to yield a pure (Z)-styryl benzylsulfide.

Part B. An ice cold solution of the (Z)-styryl benzylsulfide (3.0 g) in 30 ml of glacial acetic acid is treated with 7.5 ml of 30% hydrogen peroxide. The reaction mixture is refluxed for 1 hour and then poured on crushed ice. The separated solid is filtered, dried, and recrystalized from 2-propanol to yield the pure (Z)-styryl benzylsulfone. The purity of the compounds is ascertained by thin layer chromatography and geometrical configuration is assigned by analysis of infrared and nuclear magnetic resonance spectral data.

The bis(styryl) sulfones of formula IV are prepared according to Procedure 3:

Procedure 3

Synthesis of (E)(E)- and (E)(Z)-bis(Styryl) Sulfones

To freshly distilled phenyl acetylene (51.07 g, 0.5 mol) is added sodium thioglycollate prepared from thioglycollic acid (46 g, 0.5 mol) and sodium hydroxide (40 g, 1 mol) in methanol (250 ml). The mixture is refluxed for 24 hours and poured onto crushed ice (500 ml) after cooling. The styrylthioacetic acid, formed after neutralization with dilute hydrochloric acid (250 ml), is filtered and dried; yield 88 g (90%); m.p. 84–86° C.

The styrylthioacetic acid is then oxidized to styrylsulfonylacetic acid as follows. A mixture of styrylthioacetic acid (5 g, 25 mmol) in glacial acetic acid (35 ml) and 30% hydrogen peroxide (15 ml) is heated under reflux for 60 minutes and the mixture is poured onto crushed ice (200 ml) after cooling. The compound separated is filtered and recrystalized from hot water to give white crystalline flakes of (Z)-styrylsulfonylacetic acid; yield 2.4 g (41%); m.p. 150–51° C.

A solution of (Z)-styrylsulfonylacetic acid (2.263 g, 10 m mol) in glacial acetic acid (6 ml) is mixed with an aromatic aldehyde (10 mmol) and benzylamine (0.2 ml) and refluxed for 3 hours. The reaction mixture is cooled, treated with dry ether (50 ml), and any product separated is collected by filtration. The filtrate is diluted with more ether and washed successively with a saturated solution of sodium hydrogen carbonate (15 ml), sodium bisulfite (15 ml), dilute hydrochloric acid (20 ml) and finally with water (30 ml). Evaporation of the dried ethereal layer yields (E)(Z)-bis(styryl) sulfones.

(E),(E)-bis(styryl)sulfones are prepared following the same procedure as described above with exception that sulfonyldiacetic acid is used in place of (Z)-styrylsulfonylacetic acid, and twice the amount of aromatic aldehyde (20 mmol) is used.

The styryl sulfones of formula V, which are systematically identified as 2-(phenylsulfonyl)-1-phenyl-3-phenyl-2-propen-1-ones, may be prepared according to either Method A or Method B of Procedure 4:

Procedure 4

Synthesis of 2-(Phenylsulfonyl)-1-phenyl-3-phenyl-2-propen-1-ones

These compounds are synthesized by two methods which employ different reaction conditions, solvents and catalysts.

Method A: Phenacyl aryl sulfones are made by refluxing α-bromoacetophenones (0.05 mol) and sodium arylsulfinates (0.05 mol) in absolute ethanol (200 ml) for 6–8 hours. The product which separates on cooling is filtered and washed several times with water to remove sodium bromide. The product is then recrystalized from ethanol: phenacyl-phenyl sulfone, m.p. 90–91° C.; phenacyl-p-fluorophenyl sulfone, m.p. 148–149° C.; phenacyl-p-bromophenyl sulfone, m.p. 121–122° C.; phenacyl-p-methoxyphenyl sulfone, m.p. 104–105° C.; p-nitrophenacyl-phenyl sulfone, m.p. 136–137° C.

A solution of phenacyl aryl sulfone (0.01 mol) in acetic acid (10 ml) is mixed with an araldehyde (0.01 mol) and benzylamine (0.02 ml) and refluxed for 3 hours. The solution is cooled and dry ether (50 ml) is added. The ethereal solution is washed successively with dilute hydrochloric acid, aqueous 10% NaOH, saturated NaHSO3 solution and water. Evaporation of the dried ethereal layer gives a solid product which is purified by recrystallization.

Method B: Dry tetrahydrofuran (200 ml) is taken in a 500 ml conical flask flushed with nitrogen. To this, a solution of titanium (IV) chloride (11 ml, 0.01 mol) in absolute carbon tetrachloride is added dropwise with continuous stirring. The contents of the flask are maintained at −20° C. throughout the course of the addition. A mixture of phenacyl aryl sulfone (0.01 mol) and aromatic aldehyde (0.01 mol) is added to the reaction mixture and pyridine (4 ml, 0.04 mol) in tetrahydrofuran (8 ml) is added slowly over a period of 1 hour. The contents are stirred for 10–12 hours, treated with water (50 ml) and then ether (50 ml) is added. The ethereal layer is separated and washed with 15 ml of saturated solutions of 10% sodium hydroxide, sodium bisulfite and brine. The evaporation of the dried ethereal layer yields 2-(phenylsulfonyl)-1-phenyl-3-phenyl-2propen-1-ones.

The practice of the invention is illustrated by the following non-limiting examples. The synthesis of various $\alpha,\beta$ unsaturated aryl sulfone active agents, for use as radioprotective agents according to the practice of the invention, is set forth as "Synthesis Examples". Other material is contained in "Examples".

Synthesis examples 1 through 19. The compounds listed in Table 4 were synthesized from the reactants indicated in the table according to Procedure 1, Part B. The yields of each synthesis reaction and the melting point of the compounds produced in synthesis examples 1 through 19 are listed in Table 5. Infrared and nuclear magnetic resonance spectroscopy analyses of the compounds of synthesis examples 1 through 19 are set forth in Table 6.

TABLE 4

| Syn. Ex. | Compound | Reactant 1 (0.01 mol) | Reactant 2 (0.01 mol) |
|---|---|---|---|
| 1 | (E)-styryl phenyl sulfone | phenyl sulfonylacetic acid | benzaldehyde |
| 2 | (E)-4-chlorostyryl phenyl sulfone | phenyl sulfonylacetic acid | 4-chlorobenzaldehyde |
| 3 | (E)-2,4-dichlorostyryl phenyl sulfone | phenyl sulfonylacetic acid | 2,4-dichlorobenzaldehyde |
| 4 | (E)-4-bromostyryl phenyl sulfone | phenyl sulfonylacetic acid | 4-bromobenzaldehyde |
| 5 | (E)-4-chlorostyryl 4-chlorophenyl sulfone | 4-chlorophenyl sulfonylacetic acid | 4-chlorobenzaldehyde |
| 6 | (E)-4-methylstyryl 4-chlorophenyl sulfone | 4-chlorophenyl sulfonylacetic acid | 4-methylbenzaldehyde |
| 7 | (E)-4-methoxystyryl 4-chlorophenyl sulfone | 4-chlorophenyl sulfonylacetic acid | 4-methoxybenzaldehyde |
| 8 | (E)-4-bromostyryl 4-chlorophenyl sulfone | 4-chlorophenyl sulfonylacetic acid | 4-bromobenzaldehyde |
| 9 | (E)-2-chlorostyryl benzyl sulfone | benzyl sulfonylacetic acid | 2-chlorobenzaldehyde |
| 10 | (E)-4-chlorostyryl benzyl sulfone | benzyl sulfonylacetic acid | 4-chlorobenzaldehyde |
| 11 | (E)-4-fluorostyryl 4-chlorobenzyl sulfone | 4-chlorobenzyl sulfonylacetic acid | 4-fluorobenzaldehyde |
| 12 | (E)-4-chlorostyryl 4-chlorobenzyl sulfone | 4-chlorobenzyl sulfonylacetic acid | 4-chlorobenzaldehyde |
| 13 | (E)-4-fluorostyryl 4-fluorobenzyl sulfone | 4-fluorobenzyl sulfonylacetic acid | 4-fluorobenzaldehyde |
| 14 | (E)-2,4-difluorostyryl 4-fluorobenzyl sulfone | 4-fluorobenzyl sulfonylacetic acid | 2,4-difluorobenzaldehyde |
| 15 | (E)-4-fluorostyryl 4-bromobenzyl sulfone | 4-bromobenzyl sulfonylacetic acid | 4-fluorobenzaldehyde |
| 16 | (E)-4-bromostyryl 4-bromobenzyl sulfone | 4-bromobenzyl sulfonylacetic acid | 4-bromobenzaldehyde |
| 17 | (E)-bromostyryl 4-fluorobenzyl sulfone | 4-fluorobenzyl sulfonylacetic acid | 4-bromobenzaldehyde |
| 18 | (E)-4-chlorostyryl 4-bromobenzyl sulfone | 4-bromobenzyl sulfonylacetic acid | 4-chlorobenzaldehyde |
| 19 | (E)-4-bromostyryl 4-chlorobenzyl sulfone | 4-chlorobenzyl sulfonylacetic acid | 4-bromobenzaldehyde |

TABLE 5

| Syn. Ex. | Yield (%) | M.P. (° C.) | Compound |
|---|---|---|---|
| 1 | 68–72 | — | (E)-styryl phenyl sulfone |
| 2 | 78–80 | — | (E)-4-chlorostyryl phenyl sulfone |
| 3 | 60–65 | — | (E)-2,4-dichlorostyryl phenyl sulfone |
| 4 | 78–80 | — | (E)-4-bromostyryl phenyl sulfone |
| 5 | 70–72 | — | (E)-4-chlorostyryl 4-chlorophenyl sulfone |
| 6 | 60–64 | — | (E)-4-methylstyryl 4-chlorophenyl sulfone |
| 7 | 68–70 | — | (E)-4-methoxystyryl 4-chlorophenyl sulfone |
| 8 | 80 | — | (E)-4-bromostyryl 4-chlorophenyl sulfone |
| 9 | 72 | — | (E)-2-chlorostyryl benzyl sulfone |

TABLE 5-continued

| Syn. Ex. | Yield (%) | M.P. (° C.) | Compound |
|---|---|---|---|
| 10 | 78 | — | (E)-4-chlorostyryl benzyl sulfone |
| 11 | 72 | — | (E)-4-fluorostyryl 4-chlorobenzyl sulfone |
| 12 | 80 | — | (E)-4-chlorostyryl 4-chlorobenzyl sulfone |
| 13 | 73 | — | (E)-4-fluorostyryl 4-fluorobenzyl sulfone |
| 14 | 68 | — | (E)-2,4-difluorostyryl 4-fluorobenzyl sulfone |
| 15 | 82 | — | (E)-4-fluorostyryl 4-bromobenzyl sulfone |
| 16 | 88 | — | (E)-4-bromostyryl 4-bromobenzyl sulfone |
| 17 | 82 | — | (E)-bromostyryl 4-fluorobenzyl sulfone |
| 18 | 88 | — | (E)-4-chlorostyryl 4-bromobenzyl sulfone |
| 19 | 92 | — | (E)-4-bromostyryl 4-chlorobenzyl sulfone |

TABLE 6

IR and NMR Spectroscopy

| Syn. Ex. | IR (KR pellet) vC=C | vSO$_2$ | NMR (CDCl$_3$) (δ ppm) |
|---|---|---|---|
| 1 | 1638 | 1380, 1140 | 6.81(1H, d, J$_{H,H}$=15.6), 7.2–7.8(m, 10H), 7.49(1H, d) |
| 2 | 1627 | 1368, 1155 | 6.88(1H, d, J$_{H,H}$=15.2), 7.15–7.9(m, 9h), 7.54(1H, d) |
| 3 | 1635 | 1370, 1140 | 6.92(1H, d, J$_{H,H}$=15.6), 7.3–7.85(m, 9H), 7.62(1H, d) |
| 4 | 1642 | 1355, 1142 | 6.90(1H, d, J$_{H,H}$=15.4), 7.25–7.9(m, 9H), 7.58(1H, d) |
| 5 | 1645 | 1328, 1126 | 6.86(1H, d, J$_{H,H}$=15.6), 7.30–7.75(m, 8H), 7.55(1H, d) |
| 6 | 1650 | 1344, 1116 | 2.45(3H, s), 6.83(1H, d, J$_{H,H}$=15.8), 7.25–7.85(m, 8H), 7.48(1H, d) |
| 7 | 1658 | 1320, 1128 | 3.85(3H, s), 6.85(1H, d, J$_{H,H}$=15.4), 7.28–7.82(m, 8H), 7.60(1H, d) |
| 8 | 1660 | 1311, 1148 | 6.84(1H, d, J$_{H,H}$=15.6), 7.25–7.8(m, 8H), 7.60(1H, d) |
| 9 | 1638 | 1318, 1140 | 4.30(2H, s), 6.81(1H, d, J$_{H,H}$=15.6), 7.30–7.75(m, 9H), 7.58(1H) |
| 10 | 1642 | 1312, 1140 | 4.34(2H, s), 6.78(1H, d, J$_{H,H}$=15.7), 7.26–7.85(m, 9H), 7.54(1H) |
| 11 | 1650 | 1305, 1150 | 4.32(2H, s), 6.82(1H, d, J$_{H,H}$=16.0), 7.22–7.76(m, 8H), 7.52(1H) |
| 12 | 1658 | 1316, 1132 | 4.38(2H, s)6.86(1H, d, J$_{H,H}$=16.2), 7.26–7.85(m, 8H), 7.58(1H) |
| 13 | 1640 | 1307, 1132 | 4.44(2H, s), 6.84(1H, d, J$_{H,H}$=15.8), 7.20–7.78(m, 8H), 7.58(1H) |
| 14 | 1646 | 1326, 1145 | 4.40(2H, s), 6.88(1H, d, J$_{H,H}$=15.6), 7.33–7.72(m, 7H), 7.58(1H) |
| 15 | 1660 | 1330, 1144 | 4.46(2H, s), 6.90(1H, d, J$_{H,H}$=16.2), 7.24–7.78(m, 8H), 7.58(1H) |
| 16 | 1658 | 1316, 1132 | 4.38(2H, s), 6.76(1H, d, J$_{H,H}$=16.3), 7.36–7.84(m, 8H), 7.58(1H) |
| 17 | 1644 | 1314, 1152 | 4.43(2H, s), 6.84(1H, d, J$_{H,H}$=15.8), 7.28–7.76(m, 8H), 7.60(1H) |
| 18 | 1652 | 1321, 1148 | 4.42(2H, s), 6.78(1H, d, J$_{H,H}$=16.0), 7.34–7.80(m, 8H), 7.54(1H) |
| 19 | 1638 | 1330, 1138 | 4.38(2H, s), 6.82(1H, d, J$_{H,H}$=15.6), 7.28–7.78(m, 8H), 7.55(1H) |

Synthesis examples 20 through 37. The compounds listed in Table 7 were synthesized from the reactants indicated in the table according to Procedure 1, Part B. The yields of each synthesis reaction and the melting point of the compounds produced in synthesis examples 20 through 37 are listed in

TABLE 7

| Syn. Ex. | Compound | Reactant 1 (0.01 mol) | Reactant 2 |
|---|---|---|---|
| 20 | (E)-4-fluorostyryl-4-trifluoromethylbenzylsulfone | 4-trifluoromethylbenzyl sulfonylacetic acid | 4-fluorobenzaldehyde (0.01 mol) |
| 21 | (E)-4-chlorostyryl-4-trifluoromethylbenzylsulfone | 4-trifluoromethylbenzyl sulfonylacetic acid | 4-chlorobenzaldehyde (0.01 mol) |
| 22 | (E)-4-bromostyryl-4-trifluoromethylbenzylsulfone | 4-trifluoromethylbenzyl sulfonylacetic acid | 4-bromobenzaldehyde (0.01 mol) |
| 23 | (E)-4-fluorostyryl-2,4-dichlorobenzylsulfone | 2,4-dichlorobenzyl sulfonyl acid | 4-fluorobenzaldehyde (0.01 mol) |
| 24 | (E)-4-chlorostyryl-2,4-dichlorobenzylsulfone | 2,4-dichlorobenzyl sulfonyl acid | 4-chlorobenzaldehyde (0.01 mol) |
| 25 | (E)-4-fluorostyryl-3,4-dichlorobenzylsulfone | 3,4-dichlorobenzyl sulfonylacetic acid | 4-fluorobenzaldehyde (0.01 mol) |
| 26 | (E)-4-chlorostyryl-3,4-dichlorobenzylsulfone | 3,4-dichlorobenzyl sulfonylacetic acid | 4-chlorobenzaldehyde (0.01 mol) |
| 27 | (E)-4-bromostyryl-3,4-dichlorobenzylsulfone | 3,4-dichlorobenzyl sulfonylacetic acid | 4-bromobenzaldehyde (0.01 mol) |
| 28 | (E)-4-bromostyryl-4-nitrobenzylsulfone | 4-nitrobenzyl sulfonylacetic acid | 4-bromobenzaldehyde (0.01 mol) |
| 29 | (E)-4-fluorostyryl-4-cyanobenzylsulfone | 4-cyanobenzyl sulfonylacetic acid | 4-fluorobenzaldehyde (0.01 mol) |
| 30 | (E)-4-chlorostyryl-4-cyanobenzylsulfone | 4-cyanobenzyl sulfonylacetic acid | 4-chlorobenzaldehyde (0.01 mol) |
| 31 | (E)-4-bromostyryl-4-cyanobenzylsulfone | 4-cyanobenzyl sulfonylacetic acid | 4-bromobenzaldehyde (0.01 mol) |
| 32 | (E)-3,4-difluorostyryl-4-chlorobenzylsulfone | 4-chlorobenzyl sulfonylacetic acid | 3,4-difluorobenzaldehyde |
| 33 | (E)-3-chloro-4-fluorostyryl-4-chlorobenzylsulfone | 4-chlorobenzyl sulfonylacetic acid | 3-chloro-4-fluorobenzaldehyde |
| 34 | (E)-2-chloro-4-fluorostyryl-4-chlorobenzylsulfone | 4-chlorobenzyl sulfonylacetic acid | 2-chloro-4-fluorobenzaldehyde |
| 35 | (E)-2,4-dichlorostyryl-4-chlorobenzylsulfone | 4-chlorobenzyl sulfonylacetic acid | 2,4-dichlorobenzaldehyde |
| 36 | (E)-3,4-dichlorostyryl-4-chlorobenzylsulfone | 4-chlorobenzyl sulfonylacetic acid | 3,4-dichlorobenzaldehyde |
| 37 | (E)-2,3-dichlorostyryl-4-chlorobenzylsulfone | 4-chlorobenzylsulfonylacetic acid | 2,3-dichlorobenzaldehyde |

TABLE 8

| Syn. Ex. | Yield (%) | M.P. (° C.) | Compound |
|---|---|---|---|
| 20 | 82 | 166–168 | (E)-4-fluorostyryl-4-trifluoromethylbenzylsulfone |
| 21 | 88 | 164–168 | (E)-4-chlorostyryl-4-trifluoromethylbenzylsulfone |
| 22 | 85 | 181–183 | (E)-4-bromostyryl-4-trifluoromethylbenzylsulfone |
| 23 | 78 | 146–148 | (E)-4-fluorostyryl-2,4-dichlorobenzylsulfone |
| 24 | 84 | 148–149 | (E)-4-chlorostyryl-2,4-dichlorobenzylsulfone |
| 25 | 82 | 120–122 | (E)-4-fluorostyryl-3,4-dichlorobenzylsulfone |
| 26 | 86 | 149–151 | (E)-4-chlorostyryl-3,4-dichlorobenzylsulfone |
| 27 | 84 | 154–155 | (E)-4-bromostyryl-3,4-dichlorobenzylsulfone |
| 28 | 76 | 160–161 | (E)-4-bromostyryl-4-nitrobenzylsulfone |
| 29 | 82 | 150–151 | (E)-4-fluorostyryl-4-cyanobenzylsulfone |
| 30 | 86 | 173–177 | (E)-4-chlorostyryl-4-cyanobenzylsulfone |
| 31 | 77 | 183–184 | (E)-4-bromostyryl-4-cyanobenzylsulfone |
| 32 | 73 | 204–205 | (E)-3,4-difluorostyryl-4-chlorobenzylsulfone |
| 33 | 78 | 181–183 | (E)-3-chloro-4-fluorostyryl-4-chlorobenzylsulfone |
| 34 | 68 | 149–150 | (E)-2-chloro-4-fluorostyryl-4-chlorobenzylsulfone |
| 35 | 78 | 164–165 | (E)-2,4-dichlorostyryl-4-chlorobenzylsulfone |
| 36 | 73 | 170–171 | (E)-3,4-dichlorostyryl-4-chlorobenzylsulfone |
| 37 | 72 | 170–171 | (E)-2,3-dichlorostyryl-4-chlorobenzylsulfone |

Synthesis examples 38 through 57. The compounds listed in Table 9 were synthesized from the reactants indicated in the table by first forming the corresponding sulfide according to Procedure 2, Part A, and then oxidizing the sulfide to the sulfone according to Procedure 2, Part B. Metallic sodium (0.02 g atom) was present in each synthesis reaction. The yields of each synthesis reaction and nuclear magnetic resonance spectroscopy analyses of the compounds produced in synthesis examples 38 through 57 are listed in Table 10.

TABLE 9

| Syn. Ex. | Compound | Reactant 1 (0.02 mol) | Reactant 2 (0.02 mol) |
|---|---|---|---|
| 38 | (Z)-styryl benzylsulfone | phenylacetylene | benzyl mercaptan |
| 39 | (Z)-styryl 4-chlorobenzylsulfone | phenylacetylene | 4-chlorobenzyl mercaptan |
| 40 | (Z)-styryl 2-chlorobenzylsulfone | phenylacetylene | 2-chlorobenzyl mercaptan |
| 41 | (Z)-styryl 4-fluorobenzylsulfone | phenylacetylene | 4-fluorobenzyl mercaptan |
| 42 | (Z)-4-chlorostyryl benzylsulfone | 4-chlorophenylacetylene | benzyl mercaptan |
| 43 | (Z)-4-chlorostyryl 4-chlorobenzylsulfone | 4-chlorophenylacetylene | 4-chlorobenzyl mercaptan |
| 44 | (Z)-4-chlorostyryl 2-chlorobenzylsulfide | 4-chlorophenylacetylene | 2-chlorobenzyl mercaptan |
| 45 | (Z)-4-chlorostyryl 4-fluorobenzylsulfone | 4-chlorophenylacetylene | 4-fluorobenzyl mercaptan |
| 46 | (Z)-4-fluorostyryl benzylsulfone | 4-fluorophenylacetylene | benzyl mercaptan |
| 47 | (Z)-4-fluorostyryl 4-chlorobenzylsulfone | 4-fluorophenylacetylene | 4-chlorobenzyl mercaptan |
| 48 | (Z)-4-fluorostyryl 2-chlorobenzylsulfone | 4-fluorophenylacetylene | 2-chlorobenzyl mercaptan |
| 49 | (Z)-4-fluorostyryl 4-fluorobenzylsulfone | 4-fluorophenylacetylene | 4-fluorobenzyl mercaptan |
| 50 | (Z)-4-bromostyryl benzylsulfone | 4-bromophenylacetylene | benzyl mercaptan |
| 51 | (Z)-4-bromostyryl 4-chlorobenzylsulfone | 4-bromophenylacetylene | 4-chlorobenzyl mercaptan |
| 52 | (Z)-4-bromostyryl 2-chlorobenzylsulfone | 4-bromophenylacetylene | 2-chlorobenzyl mercaptan |
| 53 | (Z)-4-bromostyryl 4-fluorobenzylsulfone | 4-bromophenylacetylene | 4-fluorobenzyl mercaptan |
| 54 | (Z)-4-methylstyryl benzylsulfone | 4-methylphenylacetylene | benzyl mercaptan |
| 55 | (Z)-4-methylstyryl 4-chlorobenzylsulfone | 4-methylphenylacetylene | 4-chlorobenzyl mercaptan |
| 56 | (Z)-4-methylstyryl 2-chlorobenzylsulfone | 4-methylphenylacetylene | 2-chlorobenzyl mercaptan |
| 57 | (Z)-4-methylstyryl 4-fluorobenzylsulfone | 4-methylphenylacetylene | 4-fluorobenzyl mercaptan |

TABLE 10

| Syn. Ex. | Compound | Yield (%) | NMR (CDCl$_3$) (δ ppm) |
|---|---|---|---|
| 38 | (Z)-styryl benzylsulfone | 65 | 4.50(2H, s), 6.65(1H, d, $J_{H,H}$=11.2), 7.18–7.74(10H aromatic+1H ethylenic) |
| 39 | (Z)-styryl 4-chlorobenzylsulfone | 72 | 4.56(2H, s) 6.68(1H, d, $J_{H,H}$=11.8) 7.20–7.64(9H aromatic+1H ethylenic) |
| 40 | (Z)-styryl 2-chlorobenzylsulfone | 68 | 4.50(2H, s) 6.65(1H, d, $J_{H,H}$=12.0) 7.18–7.74(9H aromatic+1H ethylenic) |
| 41 | (Z)-styryl 4-fluorobenzylsulfone | 70 | 4.58(2H, s) 6.62(1H, d, $J_{H,H}$=11.86) 7.18–7.60(9H aromatic+1H ethylenic) |
| 42 | (Z)-4-chlorostyryl benzylsulfone | 74 | 4.55(2H, s) 6.66(1H, d, $J_{H,H}$=12.12) 7.16–7.65(9H aromatic+1H ethylenic) |
| 43 | (Z)-4-chlorostyryl 4-chlorobenzylsulfone | 76 | 4.62(2H, s) 6.68(1H, d, $J_{H,H}$=11.92) 7.18–7.60(8H aromatic+1H ethylenic) |
| 44 | (Z)-4-chlorostyryl 2-chlorobenzylsulfone | 73 | 4.56(2H, s) 6.70(1H, d, $J_{H,H}$=12.05) 7.18–7.64(8H aromatic+1H ethylenic) |
| 45 | (Z)-4-chlorostyryl 4-fluorobenzylsulfone | 82 | 4.60(2H, s) 6.70(1H, d, $J_{H,H}$=11.78) 7.18–7.60(8H aromatic+1H ethylenic) |
| 46 | (Z)-4-fluorostyryl benzylsulfone | 76 | 4.54(2H, s) 6.68(1H, d, $J_{H,H}$=11.94) 7.12–7.58(9H aromatic+1H ethylenic) |
| 47 | (Z)-4-fluorostyryl 4-chlorobenzylsulfone | 82 | 4.60(2H, s) 6.66(1H, d, $J_{H,H}$=11.84) 7.18–7.60(8H aromatic+1H ethylenic) |
| 48 | (Z)-4-fluorostyryl 2-chlorobenzylsulfone | 74 | 4.55(2H, s) 6.66(1H, d, $J_{H,H}$=11.94) 7.20–7.65(8H aromatic+1H ethylenic) |

TABLE 10-continued

| Syn. Ex. | Compound | Yield (%) | NMR (CDCl₃) (δ ppm) |
|---|---|---|---|
| 49 | (Z)-4-fluorostyryl 4-fluorobenzylsulfone | 78 | 4.60(2H, s)<br>6.65(1H, d, $J_{H,H}$=11.83)<br>7.20–7.65(8H aromatic+1H ethylenic) |
| 50 | (Z)-4-bromostyryl benzylsulfone | 80 | 4.52(2H, s)<br>6.80(1H, d, $J_{H,H}$=11.98)<br>7.18–7.59(9H aromatic+1H ethylenic) |
| 51 | (Z)-4-bromostyryl 4-chlorobenzylsulfone | 87 | 4.58(2H, s)<br>6.72(1H, d, $J_{H,H}$=12.08)<br>7.15–7.68(8H aromatic+1H ethylenic) |
| 52 | (Z)-4-bromostyryl 2-chlorobenzylsulfone | 84 | 4.57(2H, s)<br>6.70(1H, d, $J_{H,H}$=11.58)<br>7.18–7.58(8H aromatic+1H ethylenic) |
| 53 | (Z)-4-bromostyryl 4-fluorobenzylsulfone | 78 | 4.58(2H, s)<br>6.65(1H, d, $J_{H,H}$=11.78)<br>7.22–7.67(8H aromatic+1H ethylenic) |
| 54 | (Z)-4-methylstyryl benzylsulfone | 70 | 2.48(3H, s)<br>4.60(2H, s)<br>6.68(1H, d, $J_{H,H}$=11.94)<br>7.20–7.65(9H aromatic+1H ethylenic) |
| 55 | (Z)-4-methylstyryl benzylsulfone | 74 | 2.46(3H, s)<br>4.64(2H, s)6.75(1H, d, $J_{H,H}$=12.21)<br>7.18–7.57(9H aromatic+1H ethylenic) |
| 56 | (Z)-4-methylstyryl 2-chlorobenzylsulfone | 76 | 2.50(3H, s)<br>4.58(2H, s)<br>6.80(1H, d, $J_{H,H}$=11.88)<br>7.20–7.63(9H aromatic+1H ethylenic) |
| 57 | (Z)-4-methylstyryl 4-fluorobenzylsulfone | 69 | 2.46(3H, s)<br>4.62(2H, s)<br>6.78(1H, d, $J_{H,H}$=11.98)<br>17.18–7.59(9H aromatic+1H ethylenic) |

Synthesis examples 58 through 137. The following additional (E)-α,β unsaturated aryl sulfones listed in Tables 11a and 11b were prepared by reacting the appropriate benzylsulfonyl acetic acid and benzaldehyde or arylaldehyde according to Procedure 1, Part B.

TABLE 11a

| Syn. Ex. | M.P. (° C.) | Yield (%) | Compound |
|---|---|---|---|
| 58 | 134–136 | 55 | (E)-2-nitrostyryl-4-fluorobenzylsulfone |
| 59 | 170–173 | 64 | (E)-3-nitrostyryl-4-fluorobenzylsulfone |
| 60 | 151–152 | 61 | (E)-4-nitrostyryl-4-fluorobenzylsulfone |
| 61 | 96–98 | 54 | (E)-2-trifluoromethylstyryl-4-fluorobenzylsulfone |
| 62 | 117–119 | 55 | (E)-3-trifluoromethylstyryl-4-fluorobenzylsulfone |
| 63 | 125–128 | 73 | (E)-4-trifluoromethylstyryl-4-fluorobenzylsulfone |
| 64 | 108–112 | 52 | (E)-2-trifluoromethyl-4-fluorostyryl-4-fluorobenzylsulfone |
| 65 | 128–132 | 58 | (E)-2-nitrostyryl-4-chlorobenzylsulfone |
| 66 | 156–157 | 60 | (E)-3-nitrostyryl-4-chlorobenzylsulfone |
| 67 | 189–191 | 61 | (E)-4-nitrostyryl-4-chlorobenzylsulfone |
| 68 | 100–101 | 55 | (E)-2-trifluoromethylstyryl-4-chlorobenzylsulfone |
| 69 | 155–157 | 58 | (E)-3-trifluoromethylstyryl-4-chlorobenzylsulfone |
| 70 | 164–166 | 59 | (E)-4-trifluoromethylstyryl-4-chlorobenzylsulfone |
| 71 | 115–117 | 63 | (E)-2-trifluoromethyl-4-fluorostyryl-4-chlorobenzylsulfone |
| 72 | 169–171 | 63 | (E)-3-methyl-4-fluorostyryl-4-chlorobenzylsulfone |
| 73 | 136–138 | 57 | (E)-2-nitrostyryl-2,4-dichlorobenzylsulfone |
| 74 | 136–138 | 57 | (E)-2-trifluoromethyl-4-fluorostyryl-2,4-dichlorobenzylsulfone |
| 75 | 131–132 | 63 | (E)-2-nitrostyryl-4-bromobenzylsulfone |
| 76 | 168–170 | 56 | (E)-3-nitrostyryl-4-bromobenzylsulfone |
| 77 | 205–207 | 67 | (E)-4-nitrostyryl-4-bromobenzylsulfone |
| 78 | 102–104 | 57 | (E)-2-trifluoromethylstyryl-4-bromobenzylsulfone |
| 79 | 160–161 | 55 | (E)-3-trifluoromethylstyryl-4-fluorobenzylsulfone |
| 80 | 174–175 | 62 | (E)-4-trifluoromethylstyryl-4-bromobenzylsulfone |
| 81 | 167–168 | 63 | (E)-2-nitrostyryl-4-cyanobenzylsulfone |
| 82 | 192–193 | 62 | (E)-3-nitrostyryl-4-cyanobenzylsulfone |
| 83 | 219–220 | 66 | (E)-4-nitrostyryl-4-cyanobenzylsulfone |
| 84 | 182–184 | 70 | (E)-4-fluorostyryl-4-methylbenzylsulfone |
| 85 | 191–192 | 70 | (E)-4-bromostyryl-4-methylbenzylsulfone |
| 86 | 128–130 | 51 | (E)-2-nitrostyryl-4-methylbenzylsulfone |
| 87 | 201–203 | 56 | (E)-3-nitrostyryl-4-methylbenzylsulfone |
| 88 | 194–195 | 57 | (E)-4-nitrostyryl-4-methylbenzylsulfone |
| 89 | 148–149 | 60 | (E)-4-fluorostyryl-4-methoxybenzylsulfone |

TABLE 11a-continued

| Syn. Ex. | M.P. (° C.) | Yield (%) | Compound |
|---|---|---|---|
| 90 | 176–177 | 66 | (E)-4-chlorostyryl-4-methoxybenzylsulfone |
| 91 | 179–181 | 60 | (E)-4-bromostyryl-4-methoxybenzylsulfone |
| 92 | 127–129 | 57 | (E)-2-nitrostyryl-4-methoxybenzylsulfone |
| 93 | 153–155 | 59 | (E)-3-nitrostyryl-4-methoxybenzylsulfone |
| 94 | 179–181 | 56 | (E)-4-nitrostyryl-4-methoxybenzylsulfone |
| 95 | 176–177 | 66 | (E)-4-chlorostyryl-4-nitrobenzylsulfone |
| 96 | 199–200 | 60 | (E)-4-fluorostyryl-4-nitrobenzylsulfone |

TABLE 11b

| Syn. Ex. | M.P. (° C.) | Yield (%) | Compound |
|---|---|---|---|
| 97 | 133–136 | 80 | (E)-2,3,4,5,6-pentafluorostyryl-4-fluorobenzylsulfone |
| 98 | 146–148 | 82 | (E)-2,3,4,5,6-pentafluorostyryl-4-chlorobenzylsulfone |
| 99 | 163–164 | 85 | (E)-2,3,4,5,6-pentafluorostyryl-4-bromobenzylsulfone |
| 100 | 133–136 | 78 | (E)-4-fluorostyryl-2,3,4,5,6-pentafluorobenzylsulfone |
| 101 | 154–155 | 80 | (E)-4-chlorostyryl-2,3,4,5,6-pentafluorobenzylsulfone |
| 102 | 176–177 | 92 | (E)-4-bromostyryl-2,3,4,5,6-pentafluorobenzylsulfone |
| 103 | 171–173 | 84 | (E)-2,3,4,5,6-pentafluorostyryl-3,4-dichlorobenzylsulfone |
| 104 | 137–139 | 84 | (E)-2,3,4,5,6-pentafluorostyryl-2,3,4,5,6-pentafluorobenzylsulfone |
| 105 | 178–181 | 51 | (E)-2,3,4,5,6-pentafluorostyryl-4-iodobenzylsulfone |
| 106 | 211–212 | 54 | (E)-2-hydroxy-3,5-dinitrostyryl-4-fluorobenzylsulfone |
| 107 | 207–209 | 52 | (E)-2-hydroxy-3,5-dinitrostyryl-4-bromobenzylsulfone |
| 108 | 204–205 | 51 | (E)-2-hydroxy-3,5-dinitrostyryl-4-chlorobenzylsulfone |
| 109 | 212–213 | 56 | (E)-2-hydroxy-3,5-dinitrostyryl-2,4-dichlorobenzylsulfone |
| 110 | 142–144 | 52 | (E)-2,4,6-trimethoxystyryl-4-methoxybenzylsulfone |
| 111 | 160–161 | 52 | (E)-3-methyl-2,4-dimethoxystyryl-4-methoxybenzylsulfone |
| 112 | 138–140 | 54 | (E)-3,4,5-trimethoxystyryl-4-methoxybenzylsulfone |
| 113 | ND | ND | (E)-3,4,5-trimethoxystyryl-2-nitro-4,5-dimethoxybenzylsulfone |
| 114 | ND | ND | (E)-2,4,6-trimethoxystyryl-2-nitro-4,5-dimethoxybenzylsulfone |
| 115 | ND | ND | (E)-3-methyl-2,4-dimethoxystyryl-2-nitro-4,5-dimethoxybenzylsulfone |
| 116 | 128–129 | 72 | (E)-2,3,4-trifluorostyryl-4-fluorobenzylsulfone |
| 117 | 141–142 | 78 | (E)-2,3,4-trifluorostyryl-4-chlorobenzylsulfone |
| 118 | 134–136 | 58 | (E)-2,6-dimethoxy-4-hydroxystyryl-4-methoxybenzylsulfone |
| 119 | 154–156 | 56 | (E)-2,3,5,6-tetrafluorostyryl-4-methoxybenzylsulfone |
| 120 | 146–148 | 66 | (E)-2,4,5-trimethoxystyryl-4-methoxybenzylsulfone |
| 121 | 154–156 | 52 | (E)-2,3,4-trimethoxystyryl-4-methoxybenzylsulfone |
| 122 | 203–205 | 56 | (E)-3-nitro-4-hydroxy-5-methoxystyryl-4-methoxybenzylsulfone |
| 123 | 139–141 | 54 | (E)-3,4-dimethoxy-6-nitrostyryl-4-methoxybenzylsulfone |
| 124 | 160–161 | 58 | (E)-3,4-dimethoxy-5-iodostyryl-4-methoxybenzylsulfone |
| 125 | 146–148 | 55 | (E)-2,6-dimethoxy-4-fluorostyryl-4-methoxybenzylsulfone |
| 126 | ND | ND | (E)-2-hydroxy-4,6-dimethoxystyryl-4-methoxybenzylsulfone |
| 127 | 97–99 | 51 | (E)-2,4,6-trimethylstyryl-4-methoxybenzylsulfone |
| 128 | 181–183 | 54 | (E)-2,4,6-trimethoxystyryl-4-chlorobenzylsulfone |
| 129 | 119–121 | 55 | (E)-2,6-dimethoxy-4-fluorostyryl-4-chlorobenzylsulfone |
| 130 | ND | ND | (E)-2-hydroxy-4,6-dimethoxystyryl-4-chlorobenzylsulfone |
| 131 | 178–181 | 54 | (E)-2,4,6-trimethoxystyryl-4-bromobenzylsulfone |
| 132 | 116–118 | 58 | (E)-2,6-dimethoxy-4-fluorostyryl-4-bromobenzylsulfone |
| 133 | 94–96 | 52 | (E)-2,4,6-trimethoxystyryl-2,3,4-trimethoxybenzylsulfone |
| 134 | 110–112 | 54 | (E)-2,6-dimethoxystyryl-2,3,4-trimethoxybenzylsulfone |
| 135 | 151–153 | 54 | (E)-2,4,6-trimethoxystyryl-,3,4,5-trimethoxybenzylsulfone |
| 136 | 146–149 | 53 | (E)-2,6-dimethoxystyryl-3,4,5-trimethoxybenzylsulfone |
| 137 | 96–99 | 68 | (E)-4-fluorostyryl-2,3,4-trimethoxybenzylsulfone |

ND = Not determined.

Synthesis examples 138 through 210. Examples of further (E)-α,β unsaturated aryl sulfone compounds according to formula 1a, below, are provided in Table 12. In each compound, one of $Q_1$ or $Q_2$ is other than phenyl or substituted phenyl. Each compound was prepared by reacting the appropriate benzylsulfonyl acetic acid or (aryl)methyl sulfonyl acetic acid with the appropriate benzaldehyde or arylaldehyde according to Procedure 1, Part B. 3-Thiophene-1,1-dioxoethenyl compounds were prepared from the corresponding 3-thiopheneethenyl compound by refluxing a solution of the 3-thiopheneethenyl compound in glacial acetic acid (10 ml) and 30% hydrogen peroxide (1 ml) for 1 hour, followed by pouring the cooled contents onto crushed ice (100 g). The solid material separated was filtered and recrystalized from 2-propanol.

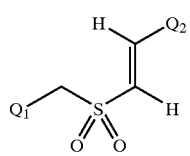

Ia

TABLE 12

| Syn. Ex. | M.P. (° C.) | % Yield | $Q_1$ | $Q_2$ |
|---|---|---|---|---|
| 138 | 110–111 | 54 | 4-fluorophenyl | 2-pyridyl |
| 139 | 155–156 | 60 | 4-fluorophenyl | 3-pyridyl |
| 140 | ND | 52 | 4-fluorophenyl | 4-pyridyl |
| 141 | 117–119 | 53 | 4-chlorophenyl | 2-pyridyl |
| 142 | 167–169 | 51 | 4-chlorophenyl | 3-pyridyl |
| 143 | 107–109 | 53 | 4-chlorophenyl | 4-pyridyl |
| 144 | 143–145 | 52 | 4-bromophenyl | 2-pyridyl |
| 145 | 161–162 | 59 | 4-bromophenyl | 3-pyridyl |
| 146 | 158–160 | 54 | 4-bromophenyl | 4-pyridyl |
| 147 | 146–148 | 53 | 4-fluorophenyl | 2-thienyl |
| 149 | 158–159 | 56 | 4-chlorophenyl | 2-thienyl |
| 149 | 169–170 | 54 | 4-bromophenyl | 2-thienyl |
| 150 | 155–157 | 54 | 4-fluorophenyl | 4-bromo-2-thienyl |
| 151 | 150–151 | 53 | 4-chlorophenyl | 4-bromo-2-thienyl |
| 152 | 154–155 | 54 | 4-bromophenyl | 4-bromo-2-thienyl |
| 153 | 161–162 | 55 | 4-fluorophenyl | 5-bromo-2-thienyl |
| 154 | 190–192 | 50 | 4-chlorophenyl | 5-bromo-2-thienyl |
| 155 | 199–200 | 52 | 4-bromophenyl | 5-bromo-2-thienyl |
| 156 | 126–128 | 52 | 4-fluorophenyl | 2-thienyl-1,1-dioxide |
| 157 | 108–110 | 55 | 4-chlorophenyl | 2-thienyl-1,1-dioxide |
| 158 | 145–147 | 56 | 4-bromophenyl | 2-thienyl-1,1-dioxide |
| 159 | 159–161 | 53 | 4-fluorophenyl | 3-thienyl |
| 160 | 169–170 | 59 | 4-chlorophenyl | 3-thienyl |
| 161 | 175–177 | 70 | 4-bromophenyl | 3-thienyl |
| 162 | 177–179 | 52 | 4-iodophenyl | 3-thienyl |
| 163 | 135–136 | 55 | 4-methylphenyl | 3-thienyl |
| 164 | 130–131 | 55 | 4-methoxyphenyl | 3-thienyl |
| 165 | 201–202 | 52 | 4-trifluoro-methylphenyl | 3-thienyl |
| 166 | 125–126 | 53 | 2,4-dichlorophenyl | 3-thienyl |
| 167 | 152–153 | 51 | 3,4-dichlorophenyl | 3-thienyl |
| 168 | 168–170 | 54 | 4-cyanophenyl | 3-thienyl |
| 169 | 203–205 | 54 | 4-nitrophenyl | 3-thienyl |
| 170 | 95–99 | 52 | 4-fluorophenyl | 3-thienyl-1,1-dioxide |
| 171 | 115–120 | 51 | 4-chlorophenyl | 3-thienyl-1,1-dioxide |
| 172 | 152–155 | 50 | 4-bromophenyl | 3-thienyl-1,1-dioxide |
| 173 | 92–95 | 54 | 4-methoxyphenyl | 3-thienyl-1,1-dioxide |
| 174 | 135–139 | 52 | 2,4-dichlorophenyl | 3-thienyl-1,1-dioxide |
| 175 | 103–105 | 53 | 4-fluorophenyl | 2-furyl |
| 176 | 106–108 | 52 | 4-chlorophenyl | 2-furyl |
| 177 | 125–127 | 52 | 4-bromophenyl | 2-furyl |
| 178 | 114–117 | 51 | 4-fluorophenyl | 3-furyl |
| 179 | 154–156 | 50 | 4-chlorophenyl | 3-furyl |
| 180 | 156–158 | 51 | 4-bromophenyl | 3-furyl |
| 181 | 166–170 | 52 | 4-iodophenyl | 3-furyl |
| 182 | 123–126 | 53 | 4-methylphenyl | 3-furyl |
| 183 | 117–119 | 51 | 4-methoxyphenyl | 3-furyl |
| 184 | 167–169 | 51 | 4-trifluoro-methylphenyl | 3-furyl |
| 185 | 104–106 | 53 | 2,4-dichlorophenyl | 3-furyl |
| 186 | 131–133 | 52 | 3,4-dichlorophenyl | 3-furyl |
| 187 | 175–178 | 53 | 4-cyanophenyl | 3-furyl |
| 188 | 210–213 | 52 | 4-nitrophenyl | 3-furyl |
| 189 | 133–137 | 51 | 4-chlorophenyl | 2-thiazolyl |
| 190 | ND | ND | 4-chlorophenyl | 2-pyrrolyl |
| 191 | ND | ND | 4-bromophenyl | 2-pyrrolyl |
| 192 | 228–230 | 56 | 4-chlorophenyl | 2-nitro-4-thienyl |
| 193 | 177–179 | 67 | 4-iodophenyl | 2-nitro-4-thienyl |
| 194 | 228–230 | 64 | 2,4-dichlorophenyl | 2-nitro-4-thienyl |
| 195 | 170–172 | 56 | 4-methoxyphenyl | 2-nitro-4-thienyl |
| 196 | 148–150 | 55 | 4-fluorophenyl | 1-naphthyl |
| 197 | 185–186 | 58 | 4-fluorophenyl | 2-naphthyl |
| 198 | 142–143 | 63 | 4-chlorophenyl | 1-naphthyl |
| 199 | 191–193 | 52 | 4-chlorophenyl | 2-naphthyl |
| 200 | 147–149 | 52 | 4-bromophenyl | 1-naphthyl |
| 201 | 193–194 | 54 | 4-bromophenyl | 2-naphthyl |
| 202 | 142–144 | 52 | 1-naphthyl | 4-fluorophenyl |
| 203 | 195–197 | 53 | 1-naphthyl | 4-chlorophenyl |
| 204 | 207–209 | 55 | 1-naphthyl | 4-bromophenyl |
| 205 | 188–192 | 62 | 1-naphthyl | 2-nitrophenyl |
| 206 | 192–194 | 59 | 1-naphthyl | 3-nitrophenyl |
| 207 | 252–254 | 61 | 1-naphthyl | 4-nitrophenyl |
| 208 | 93–95 | 56 | 4-fluorophenyl | 9-anthryl |
| 209 | 122–124 | 53 | 4-chlorophenyl | 9-anthryl |
| 210 | 172–175 | 51 | 4-bromophenyl | 9-anthryl |

Synthesis Examples 211–219. Synthesis Examples 211–213 exemplify the preparation of (E)(Z)-bis(styryl) sulfones prepared by Procedure 3. Synthesis Examples 214–219 exemplify the preparation of 2-(phenylsulfonyl)-1-phenyl-3-phenyl-2-propen-1-ones made by Procedure 4, Method 1. Reactants and title compounds are given in Table 13. Yields (and melting point for Synth. Ex. 219) are given in Table 14. Infrared and nuclear magnetic resonance spectroscopy analyses of Synth. Exs. 211–218 are given in Table 15.

TABLE 13

| Syn. Ex. | Compound | Reactant 1 (0.01 mol) | Reactant 2 (0.01 mol) |
|---|---|---|---|
| 211 | (Z)-styryl-(E)-4-fluorostyryl sulfone | (Z)-styryl sulfonylacetic acid | 4-fluorobenzaldehyde |
| 212 | (Z)-styryl-(E)-4-bromostyryl sulfone | (Z)-styryl sulfonylacetic acid | 4-bromobenzaldehyde |
| 213 | (Z)-styryl-(E)-4-chlorostyryl sulfone | (Z)-styryl sulfonylacetic acid | 4-chlorobenzaldehyde |
| 214 | 2-[(4-fluorophenyl)sulfonyl]-1-phenyl-3-(4-fluorophenyl)-2-propen-1-one | phenacyl-4-fluorophenyl sulfone | 4-fluorobenzaldehyde |
| 215 | 2-[(2-chlorophenyl)-sulfonyl]-1-phenyl-3-(4-fluorophenyl)-2-propen-1-one | phenacyl-2-chlorophenyl sulfone | 4-fluorobenzaldehyde |
| 216 | 2-[(2-chlorophenyl)sulfonyl]-1-phenyl-3-(4-bromophenyl)-2-propen-1-one | phenacyl-2-chlorophenyl sulfone | 4-bromobenzaldehyde |
| 217 | 2-[(4-chlorophenyl)sulfonyl]-1-phenyl-3-(4-bromophenyl)-2-propen-1-one | phenacyl-4-chlorophenyl sulfone | 4-bromobenzaldehyde |

TABLE 13-continued

| Syn. Ex. | Compound | Reactant 1 (0.01 mol) | Reactant 2 (0.01 mol) |
|---|---|---|---|
| 218 | 2-[(2-nitrophenyl)sulfonyl]-1-phenyl-3-(4-bromophenyl)-2-propen-1-one | phenacyl-2-nitrophenyl sulfone | 4-bromobenzaldehyde |
| 219 | 2-(phenylsulfonyl)-1-phenyl-3-(4-fluorophenyl)-2-propen-1-one | phenacylphenyl sulfone | 4-fluorobenzaldehyde |

TABLE 14

| Syn. Ex. | Yield (%) | M.P. (° C.) | Compound |
|---|---|---|---|
| 211 | 68 | — | (Z)-styryl-(E)-4-fluorostyryl sulfone |
| 212 | 70 | — | (Z)-styryl-(E)-4-bromostyryl sulfone |
| 213 | 64 | — | (Z)-styryl-(E)-4-chlorostyryl sulfone |
| 214 | 63 | — | 2-[(4-fluorophenyl)sulfonyl]-1-phenyl-3-(4-fluorophenyl)-2-propen-1-one |
| 215 | 58 | — | 2-[(2-chlorophenyl)-sulfonyl]-1-phenyl-3-(4-fluorophenyl)-2-propen-1-one |
| 216 | 66 | — | 2-[(2-chlorophenyl)sulfonyl]-1-phenyl-3-(4-bromophenyl)-2-propen-1-one |
| 217 | 60 | — | 2-[(4-chlorophenyl)sulfonyl]-1-phenyl-3-(4-bromophenyl)-2-propen-1-one |
| 218 | 56 | — | 2-[(2-nitrophenyl)sulfonyl]-1-phenyl-3-(4-bromophenyl)-2-propen-1-one |
| 219 | 62 | 142–143 | 2-(phenylsulfonyl)-1-phenyl-3-(4-fluorophenyl)-2-propen-1-one |

TABLE 15

| | IR and NMR Spectroscopy | | |
|---|---|---|---|
| 211 | — | 1300, 1120 | 6.55(1H, d, $J_{H,H}$=10.8), 6.70(1H, d, $J_{H,H}$=14.8), 7.20–7.92 (m, 9H aromatic, 2H vinyl) |
| 212 | — | 1318, 1128 | 6.68(1H, d, $J_{H,H}$=11.0), 6.86(1H, d, $J_{H,H}$=15.0), 7.15–7.90 (m, 9H aromatic, 2H vinyl) |
| 213 | — | 1330, 1100 | 6.65(1H, d, $J_{H,H}$=11.2), 6.81(1H, d, $J_{H,H}$=15.4), 7.00–7.85 (m, 9H aromatic, 2H vinyl) |
| 214 | 1620 | 1320, 1145 | 8.04(1H, s, —C=CH) 7.35–7.95(m, 13H) |
| 215 | 1625 | 1320, 1148 | 8.48(1H, s, —C=CH) 7.40–8.25(m, 13H) |
| 216 | 1618 | 1315, 1140 | 8.05(1H, s, —C=CH) 7.28–8.00(m, 13H) |
| 217 | 1620 | 1318, 1142 | 8.47(1H, s, —C=CH) 7.30–8.15(m, 13H) |
| 218 | 1618 | 1315, 1140 | 8.57(1H, s, —C=CH) 7.40–8.20(m, 13H) |

EXAMPLE 1

Radioprotective Effects of α,β-Unsaturated Arylsulfones on Cultured Normal Cells The radioprotective effects of the compounds in Table 16 below on cultured normal cells were evaluated as follows.

HFL-1 cells, which are normal diploid lung fibroblasts, were plated into 24 well dishes at a cell density of 3000 cells per 10 mm$^2$ in DMEM completed with 10% fetal bovine serum and antibiotics. The test compounds listed in Table 16 were added to the cells 24 hours later in select concentrations from 2.5 to 20 micromolar, inclusive, using DMSO as a solvent. Control cells were treated with DMSO alone. The cells were exposed to the test compound or DMSO for 24 hrs. The cells were then irradiated with either 10 Gy (gray) or 15 Gy of ionizing radiation (IR) using a J. L. Shepherd Mark I, Model 30-1 Irradiator equipped with $^{137}$cesium as a source.

After irradiation, the medium on the test and control cells was removed and replaced with fresh growth medium without the test compounds or DMSO. The irradiated cells were incubated for 96 hours and duplicate wells were trypsinized and replated onto 100 mm$^2$ tissue culture dishes. The replated cells were grown under normal conditions with one change of fresh medium for 3 weeks. The number of colonies from each 100 mm$^2$ culture dish, which represents the number of surviving cells, was determined by staining the dishes as described below.

To visualize and count the colonies derived from the clonal outgrowth of individual radioprotected cells, the medium was removed and the plates were washed one time with room temperature phosphate buffered saline. The cells were stained with a 1:10 diluted Modified Giemsa staining solution (Sigma) for 20 minutes. The stain was removed, and the plates were washed with tap water. The plates were air dried, the number of colonies from each plate were counted and the average from duplicate plates was determined.

The results are presented in Table 16. A "+" indicates radioprotective activity of between 2- and 4.5-fold at the concentrations tested. Fold protection was determined by dividing the average number of colonies from the test plates by the average number of colonies on the control plates.

TABLE 16

Radioprotection by α,β-Unsaturated Arylsulfones

| Compound Number | Chemical Name | Activity |
|---|---|---|
| 1 | (E)-4-Fluorostyryl-4-chlorobenzylsulfone | + |
| 2 | (E)-2,4,6-Trimethoxystyryl-4-methoxybenzylsulfone | + |
| 3 | (E)-2-Methoxystyryl-4-nitrobenzylsulfone | − |
| 4 | (E)-2,3,4,5,6-Pentafluorostyryl-4-methoxybenzylsulfone | − |
| 5 | (E)-4-Fluorostyryl-4-trifluoromethylbenzylsulfone | + |
| 6 | (E)-4-Fluorostyryl-4-cyanobenzylsulfone | + |
| 7 | (Z)-4-Fluorostyryl-4-chlorobenzylsulfone | + |
| 8 | (E)-3-Furanethenyl-2,4-dichlorobenzylsulfone | + |
| 9 | (E)-4-Pyridylethenyl-4-chlorobenzylsulfone | − |
| 10 | (E)-4-Fluorostyryl-4-chlorophenylsulfone | + |
| 11 | (Z)-Styryl-(E)-2-methoxy-4-ethoxystyrylsulfone | + |
| 12 | (E)-4-Hydroxystyryl-4-chlorobenzylsulfone | − |
| 13 | (E)-4-Carboxystyryl-4-chlorobenzylsulfone | + |

EXAMPLE 2

Treatment of Cultured Tumor Cells with α,β-Unsaturated Arylsulfones

A. Tumor Cell Killing by Ionizing Radiation with Pre-Treatment of Cells with α,β-Unsaturated Arylsulfones In order to address the effect of the α,β-unsaturated arylsulfones on tumor cell killing by ionizing irradiation under conditions that are protective for normal fibroblasts, the following experiments were conducted. DU145 cells, an androgen negative prostate carcinoma cell line, were plated in 6 well dishes at a cell density of $1.0 \times 10^5$ cells per 35 mm$^2$ in DMEM completed with 10% fetal bovine serum and antibiotics. Compound 1 (0.5 uM, 1.0 uM and 2.5 uM) and Compound 13 (5.0 uM, 10.0 uM and 20.0 uM) in DMSO, see Table 16 above, were added separately to the cells 24 hours later. Control cells received DMSO alone. The plates were incubated for 20–24 hours and the cells were irradiated with either 5 Gy or 10 Gy of irradiation.

After irradiation, the medium was removed and replaced with fresh medium without the test compound or DMSO. The cells were incubated for 96 hours and the number of viable cells was determined by trypan blue exclusion. The average number of viable cells from duplicate wells was determined and plotted in FIGS. 1A (Compound 1; 5 Gy), 1B (Compound 1; 10 Gy), 2A (Compound 13; 5 Gy) and 2B (Compound 13; 10 Gy). The DMSO bar indicates the number of viable control cells after DMSO treatment and no irradiation. The DMSO-RAD bar represents the number of viable control cells remaining after DMSO treatment with irradiation.

The data clearly show that the addition of the α,β unsaturated aryl sulfone that induced radioprotection in normal human lung fibroblasts did not reduce the killing activity of the ionizing radiation on the tumor cell line. A small but consistent additive affect on cell killing of the tumor cells is also seen. These data suggest that the radio-protective effect of the α,β unsaturated aryl sulfone is specific for normal tissue, and does not interfere with the killing of tumor cells by IR when the tumor cells are treated with the test compounds as a 20–24 hour pulse prior to irradiation.

B. Tumor Cell Killing by Ionizing Radiation in the Continued Presence of α,β-Unsaturated Arylsulfones Added After IR Treatment To further show that the α,β-unsaturated arylsulfones which provide radiation protection for normal cells do not interfere with tumor cell killing by IR, DU145 cells were treated with different concentrations of either Compound 1 or Compound 13 (see Table 16, above) immediately following the ionizing radiation treatment for the duration of the experiment.

Figure 3B:
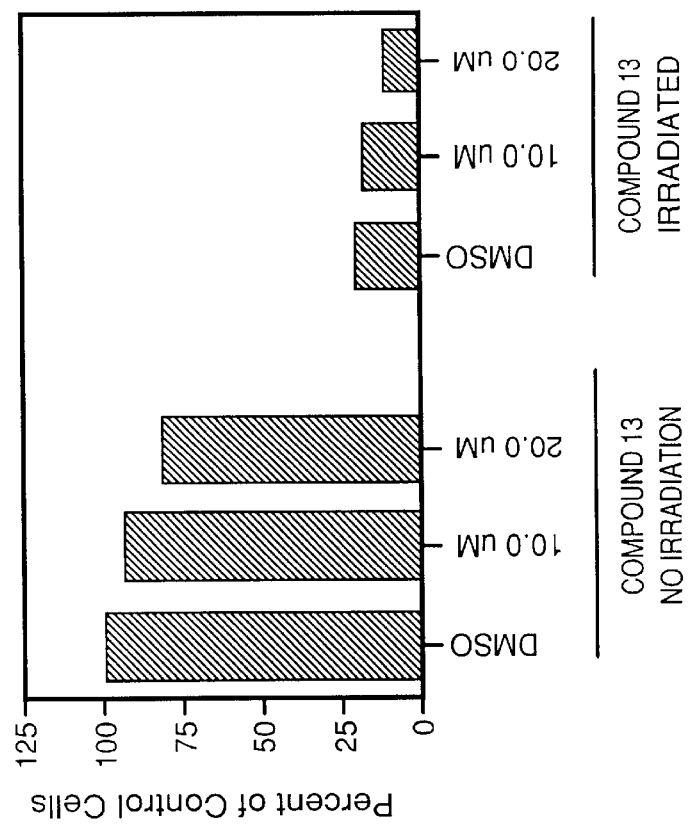
FIGS. 3A and 3B show the effect of 10 Gy ionizing radiation on the viability of DU145 prostate tumor cells treated post-irradiation, respectively, with (E)-4-fluorostyryl-4-chlorobenzylsulfone and (E)-4-carboxystyryl-4-chlorobenzylsulfone.
Figure 3A:
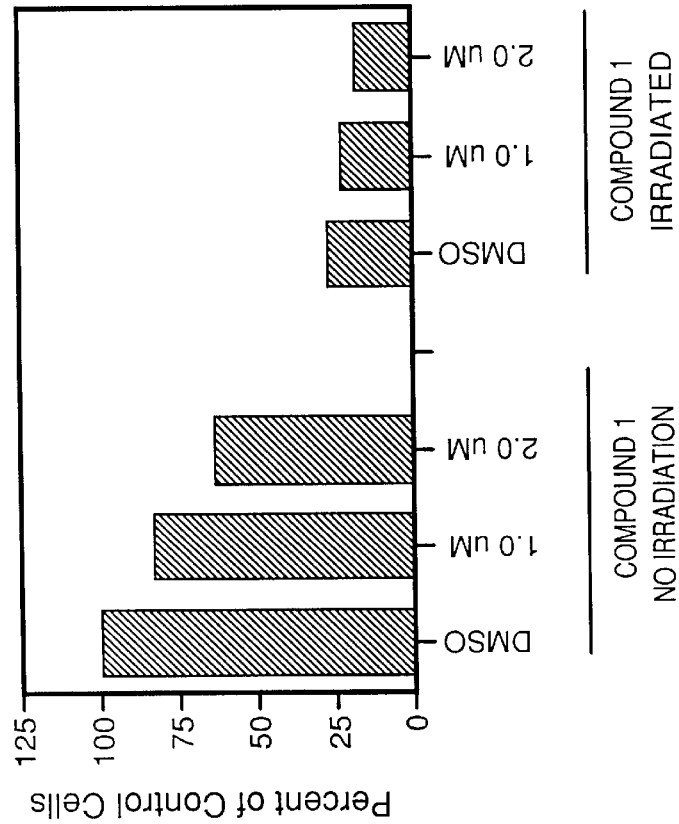

DU145 cells were plated in 6 well dishes at a cell density of $1.0 \times 10^5$ cells per 35 mm$^2$ in DMEM completed with 10% fetal bovine serum and antibiotics. The plates were incubated overnight and the cells were irradiated with 10 Gy of ionizing irradiation. Compound 1 (1.0 uM and 2.0 uM) or Compound 13 (10.0 uM and 20.0 uM) in DMSO was added to the cells immediately following the IR treatment. The total number of viable cells for each treatment was determined as described above in Example 2, part A. FIGS. 3A (Compound 1) and 3B (Compound 13) show that continuous exposure of the tumor cells to the test compounds did not interfere with the killing of tumor cells by ionizing radiation. The data also show an additive tumor cell killing effect on treatment with 2.0 uM of Compound 1 or 20 uM of Compound 13. These data suggest that styryl-benzylsulfones which exhibit radiation protection for normal cells do not interfere with tumor cell killing by ionizing radiation.

EXAMPLE 3

Toxicity of (E)-4-Fluorostyryl-4-Chlorobenzylsulfone in Mice

Figure 4:
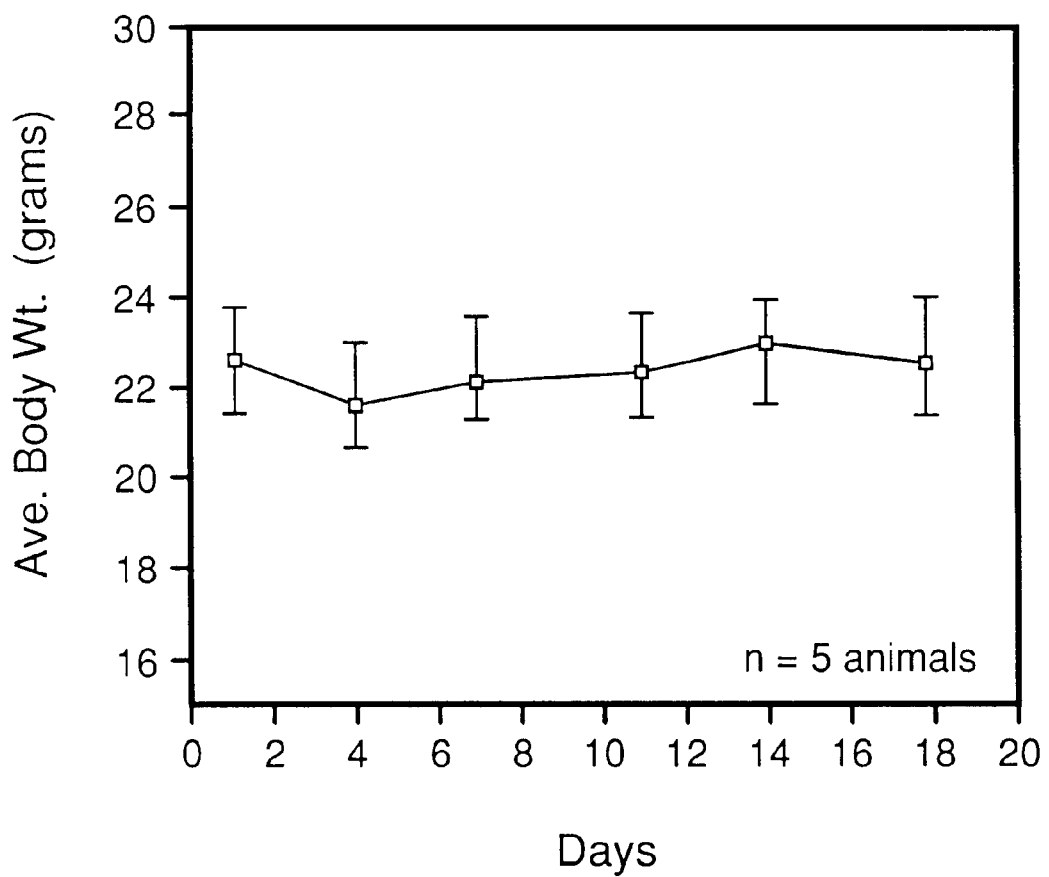
FIG. 4 is a plot of average body weight (grams) vs. time(days) for C57B6/J mice given 4 mg/kg (E)-4-fluorostyryl-4-chlorobenzylsulfone every other day for 18 days.

Five C57 B6/J mice age 10–12 weeks (Taconic) were given doses of 4 mg/kg (E)-4-fluorostyryl-4-chlorobenzylsulfone in DMSO intraperitoneally every other day for 18 days. The animals' weight and gross pathology were monitored, and no adverse effect was seen over the course of the treatment. The average body weight of the five mice (in grams) vs. time (in days) was plotted in FIG. 4, showing essentially no change in the animals' body weight throughout the experiment. These results suggest that α,β-unsaturated arylsulfones may be safely administered in the long-term.

EXAMPLE 4

Figure 5:
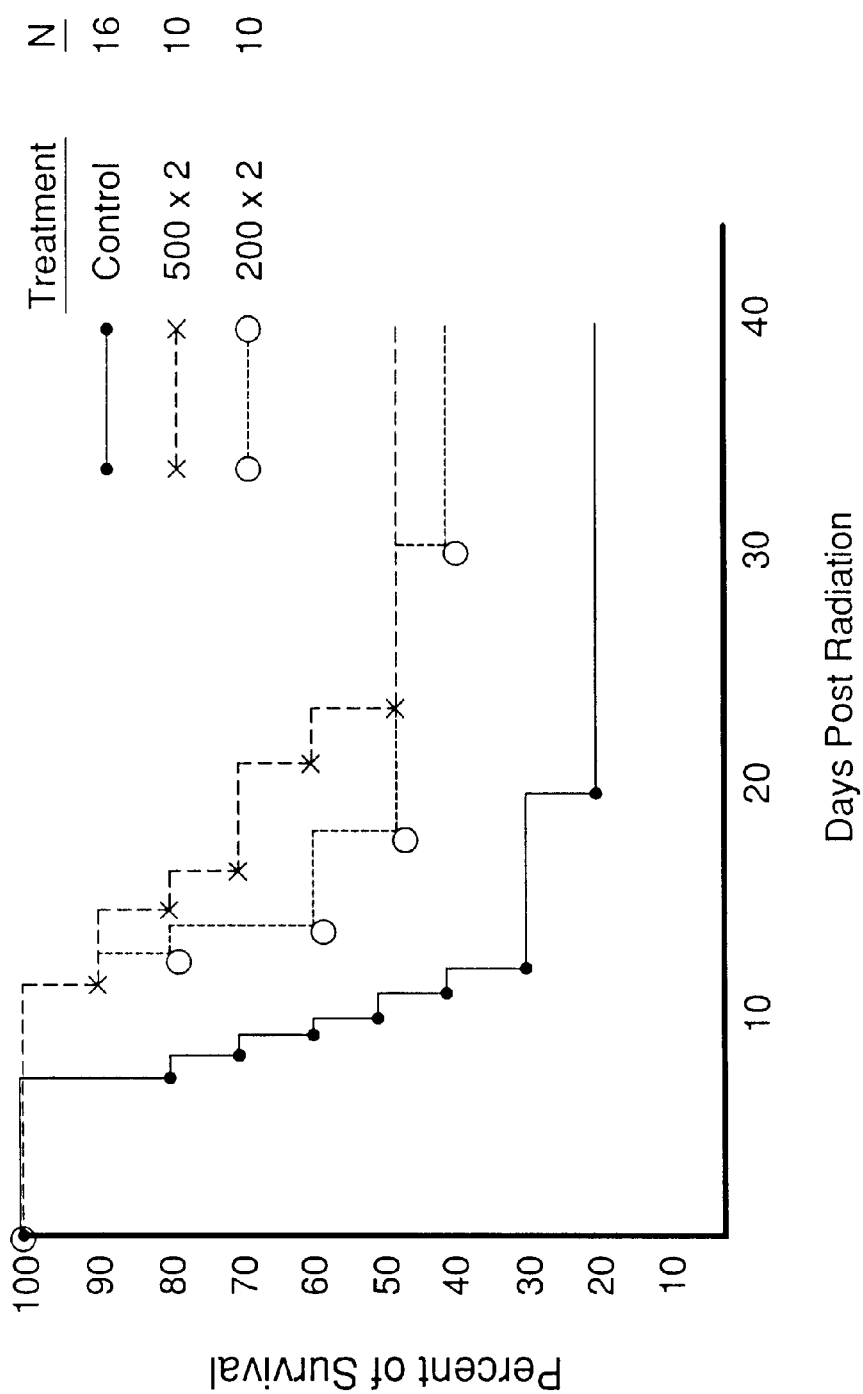
FIG. 5 is a Kaplan Meyer survival plot of C57B6/J mice pre-treated with (E)-4-carboxystyryl-4-chlorobenzylsulfone at 18 and 6 hrs before receiving 8 Gy of ionizing radiation.

Protection of Mice from Radiation Toxicity by Pre-Treatment With (E)-4-Carboxystyryl-4-Chlorobenzylsulfone C57 black mice age 10–12 weeks (Taconic) were divided into two treatment groups of 10 mice each. One group, designated the "200×2" group, received intraperitoneal injections of 200 micrograms (E)-4-carboxystyryl-4-chlorobenzylsulfone dissolved in DMSO (a 10 mg/Kg dose, based on 20 g mice) 18 and 6 hours before irradiation with 8 Gy gamma radiation. The other group, designated "500× 2," received intraperitoneal injections of 500 micrograms (E)-4-carboxystyryl-4-chlorobenzylsulfone dissolved in DMSO (a 25 mg/Kg dose, based on 20 g mice) 18 and 6 hours before irradiation with 8 Gy gamma radiation. A control group of 16 animals received 8 Gy gamma radiation alone. Mortality of control and experimental groups was assessed for 40 days after irradiation, and the results are shown in FIG. 5.

By day 20 post-irradiation, the control mice exhibited a maximum mortality rate of 80%; the 8 Gy dose of gamma radiation is thus considered an $LD_{80}$ dose. By contrast, only about 50% of the "200×2" group and about 30% of the "500×2" mice were dead at day 20 after receiving the $LD_{80}$ radiation dose. By day 40, a maximum mortality rate of approximately 60% was reached in the "200×2" group, and a maximum mortality rate of approximately 50% was reached in the "500×2" group. These data show that radiation toxicity in mice is significantly reduced by pretreatment with (E)-4-carboxystyryl-4-chlorobenzylsulfone.

EXAMPLE 5

Radioprotective Effect of (E)-4-Carboxystyryl-4-chlorobenzylsulfone in Mice When Given After Radiation Exposure C57 B6/J mice age 10–12 weeks (Taconic) were divided into two treatment groups of 10 and 9 mice, respectively. One group, designated the "200×2" group, received intraperitoneal injections of 200 micrograms (E)-4-carboxystyryl-4-chlorobenzylsulfone dissolved in DMSO (a 10 mg/Kg dose, assuming 20 g mice) 18 and 6 hours before irradiation with 8 Gy gamma radiation. The other group, designated "200 Post," received an intraperitoneal injection of 200 micrograms (E)-4-carboxystyryl-4-chlorobenzylsulfone dissolved in DMSO (a 10 mg/Kg dose, based on 20 g mice) 15 minutes after irradiation with 8 Gy gamma radiation. A control group of 16 animals received 8 Gy gamma radiation alone. Mortality of control and experimental groups was assessed for 40 days after irradiation, and the results are shown in FIG. 6.

Figure 6:
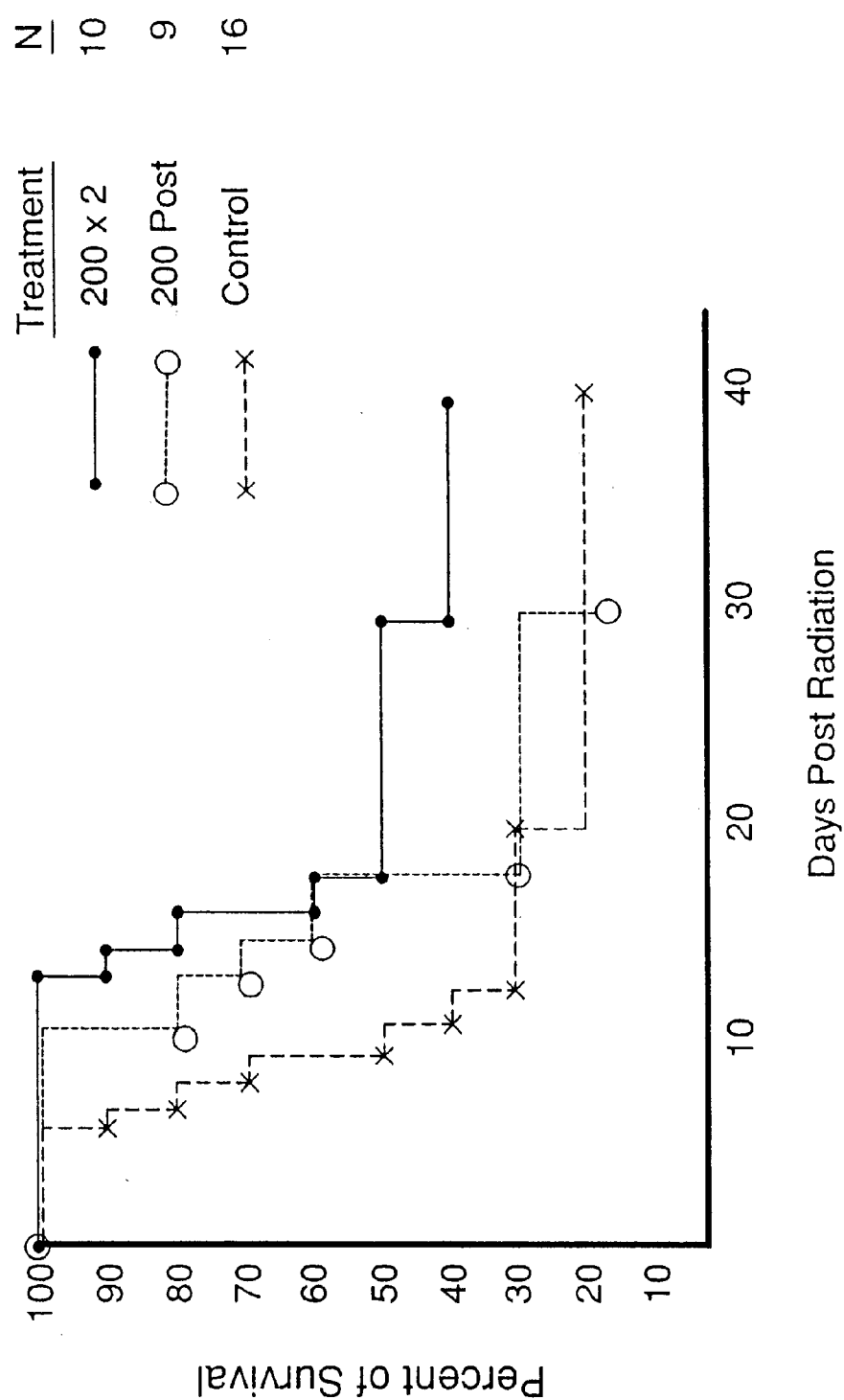
FIG. 6 is a Kaplan Meyer survival plot of C57B6/J mice treated with (E)-4-carboxystyryl-4-chlorobenzylsulfone after receiving 8 Gy of ionizing radiation.

FIG. 6 shows that treatment of mice with (E)-4-carboxystyryl-4-chlorobenzylsulfone after irradiation resulted in significant delay in radiation-induced mortality as compared with the control animals. While the radioprotection afforded by post-irradiation treatment is not as great as seen with pre-irradiation treatment, (E)-4-carboxystyryl-4-chlorobenzylsulfone is nonetheless effective in mitigating the effects of radiation toxicity after the subject has received the radiation dose.

EXAMPLE 6

Effect of Exposure to Ionizing Radiation on Normal and Malignant Hematopoietic Progenitor Cell Growth After Pretreatment with $\alpha,\beta$ Unsaturated Arylsulfones The effect of ionizing radiation on normal and malignant hematopoietic progenitor cells which are pretreated with $\alpha,\beta$ unsaturated arylsulfones is determined by assessing cloning efficiency and development of the pretreated cells after irradiation.

To obtain hematopoietic progenitor cells, human bone marrow cells (BMC) or peripheral blood cells (PB) are obtained from normal healthy, or acute or chronic myelogenous leukemia (AML, CML), volunteers by Ficoll-Hypaque density gradient centrifugation, and are partially enriched for hematopoietic progenitor cells by positively selecting $CD34^+$ cells with immunomagnetic beads (Dynal A. S., Oslo, Norway). The $CD34^+$ cells are suspended in supplemented alpha medium and incubated with mouse anti-HPCA-I antibody in 1:20 dilution, 45 minutes, at 4° C. with gentle inverting of tubes. Cells are washed×3 in supplemented alpha medium, and then incubated with beads coated with the Fc fragment of goat anti-mouse $IgG_1$ (75 $\mu$l of immunobeads/$10^7$ $CD34^+$ cells). After 45 minutes of incubation (4° C.), cells adherent to the beads are positively selected using a magnetic particle concentrator as directed by the manufacturer.

$2\times10^4$ $CD34^+$ cells are incubated in 5 ml polypropylene tubes (Fisher Scientific, Pittsburgh, Pa.) in a total volume of 0.4 ml of Iscove's modified Dulbecco's medium (IMDM) containing 2% human AB serum and 10 mM Hepes buffer. An $\alpha,\beta$ unsaturated arylsulfone is added to the cells; for example, (E)-4-fluorostyryl-4-chlorobenzyl-sulfone in three different concentrations (0.5 uM, 1.0 uM and 2.5 uM) or (E)-4-carboxystyryl-4-chlorobenzylsulfone in three different concentrations (5.0 uM, 10.0 uM and 20.0 uM) in DMSO are added separately to the cells. Control cells received DMSO alone. The cells are incubated for 20–24 hours and irradiated with 5 Gy or 10 Gy of ionizing radiation.

Immediately after irradiation, the medium is removed and replaced with fresh medium without the test compound or DMSO. Twenty-four hours after irradiation, the treatment and control cells are prepared for plating in plasma clot or methylcellulose cultures. Cells ($1\times10^4$ $CD34^+$ cells per dish) are not washed before plating.

Assessment of the cloning efficiency and development of the treated hematopoietic progenitor cells are carried out essentially as reported in Gewirtz et al., Science 242, 1303–1306 (1988), the disclosure of which is incorporated herein by reference.

EXAMPLE 7

Bone Marrow Purging with Ionizing Radiation After Pretreatment with $\alpha,\beta$ Unsaturated Arylsulfones Bone marrow is harvested from the iliac bones of a subject under general anesthesia in an operating room using standard techniques. Multiple aspirations are taken into heparinized syringes. Sufficient marrow is withdrawn so that the subject will be able to receive about $4\times10^8$ to about $8\times10^8$ processed marrow cells per kg of body weight. Thus, about 750 to 1000 ml of marrow is withdrawn. The aspirated marrow is transferred immediately into a transport medium (TC-199, Gibco, Grand Island, N.Y.) containing 10,000 units of preservative-free heparin per 100 ml of medium. The aspirated marrow is filtered through three progressively finer meshes to obtain a cell suspension devoid of cellular aggregates, debris and bone particles. The filtered marrow is then processed further into an automated cell separator (e.g., Cobe 2991 Cell Processor) which prepares a "buffy coat" product, (i.e., leukocytes devoid of red cells and platelets). The buffy coat preparation is then placed in a transfer pack for further processing and storage. It may be stored until purging in liquid nitrogen using standard procedures. Alternatively, purging can be carried out immediately, then the purged marrow may be stored frozen in liquid nitrogen until it is ready for transplantation.

The purging procedure is carried out as follows. Cells in the buffy coat preparation are adjusted to a cell concentration of about $2\times10^7$/ml in TC-199 containing about 20% autologous plasma. An $\alpha,\beta$ unsaturated arylsulfone; for example, 1–2 micromolar of (E)-4-fluorostyryl-4-chlorobenzylsulfone in DMSO or 10–20 micromolar (E)-4-carboxystyryl-4-chlorobenzylsulfone in DMSO is added to the transfer packs containing the cell suspension and incubated in a 37° C. waterbath for 20–24 hours with gentle shaking. The transfer packs are then exposed to 5–10 Gy ionizing radiation. Recombinant human hematopoietic growth factors, e.g., rH IL-3 or rH GM-CSF, may be added to the suspension to stimulate growth of hematopoietic neoplasms and thereby increase their sensitivity to ionizing radiation.

The cells may then either be frozen in liquid nitrogen or washed once at 4° C. in TC-199 containing about 20% autologous plasma. Washed cells are then infused into the subject. Care must be taken to work under sterile conditions wherever possible and to maintain scrupulous aseptic techniques at all times.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A method of reducing or eliminating the effects of ionizing radiation on normal cells in a subject who has incurred or is at risk for incurring exposure to ionizing radiation, comprising administering to the subject an effective amount of at least one radioprotective α,β unsaturated aryl sulfone compound prior to or after exposure to ionizing radiation.

2. The method of claim 1 wherein the radioprotective compound has the formula I:

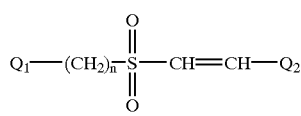

wherein:
n is one or zero;
$Q_1$ and $Q_2$ are, same or different, are substituted or unsubstituted aryl, or substituted or unsubstituted heteroaryl; or
a pharmaceutically acceptable salt thereof.

3. The method of claim 2 wherein the radioprotective compound is (E)-3-furanethenyl-2,4-dichlorobenzylsulfone.

4. The method of claim 2 wherein $Q_1$, $Q_2$, or both are selected from substituted and unsubstituted phenyl.

5. The method of claim 4 wherein the radioprotective compound has the formula II:

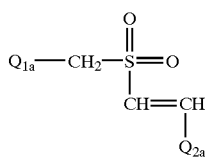

wherein:
$Q_{1a}$ and $Q_{2a}$ are independently selected from the group consisting of phenyl and mono-, di-, tri-, tetra- and penta-substituted phenyl where the substituents, which may be the same or different, are independently selected from the group consisting of hydrogen, halogen, C1–C8 alkyl, C1–C8 alkoxy, nitro, cyano, carboxy, hydroxy, phosphonato, amino, sulfamyl, acetoxy, dimethylamino(C2–C6 alkoxy), C1–C6 trifluoroalkoxy and trifluoromethyl.

6. The method of claim 5, wherein $Q_{1a}$ is 4-alkoxyphenyl and $Q_{2a}$ is 2,4,6-trialkoxyphenyl.

7. The method of claim 6, wherein the radioprotective compound is (E)-2,4,6-trimethoxystyryl-4-methoxybenzylsulfone.

8. The method of claim 5 wherein the radioprotective compound has the formula III:

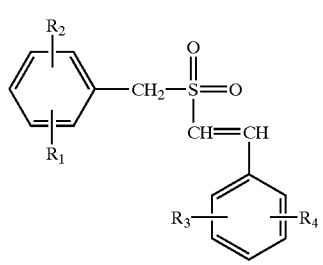

wherein $R_1$, $R_2$, $R_3$ and $R_4$ are independently selected from the group consisting of hydrogen, halogen, C1–C8 alkyl, C1–C8 alkoxy, nitro, cyano, carboxy, hydroxy, phosphonato, amino, sulfamyl, acetoxy, dimethylamino(C2–C6 alkoxy), C1–C6 trifluoroalkoxy and trifluoromethyl or a pharmaceutically acceptable salt thereof.

9. The method of claim 8 wherein the radioprotective compound has the formula IIIa:

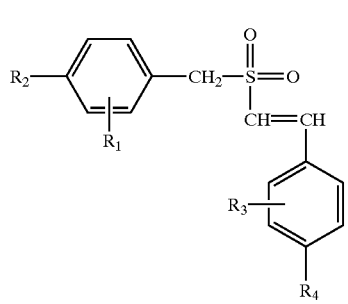

wherein $R_2$ and $R_4$ are other than hydrogen.

10. The method of claim 9 wherein the radioprotective compound is selected from the group consisting of (E)-4-fluorostyryl-4-chlorobenzylsulfone, (E)-4-fluorostyryl-4-trifluoromethylbenzylsulfone, (E)-4-fluorostyryl-4-cyanobenzylsulfone, (Z)-4-fluorostyryl-4-chlorobenzylsulfone, (E)-4-fluorostyryl-4-chlorophenylsulfone and (E)-4-carboxystyryl-4-chlorobenzylsulfone.

11. The method of claim 1 wherein the radioprotective compound is according to formula IV:

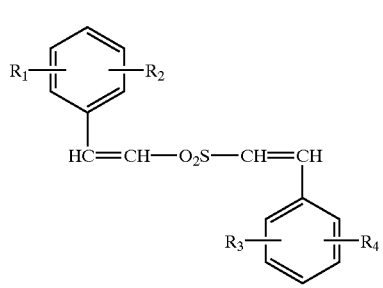

wherein:
$R_1$, $R_2$, $R_3$ and $R_4$ are independently selected from the group consisting of hydrogen, halogen, C1–C8 alkyl, C1–C8 alkoxy, nitro, cyano, carboxy, hydroxy and trifluoromethyl;
or a pharmaceutically acceptable salt thereof.

12. The method of claim 11, wherein the radioprotective compound is (Z)-styryl-(E)-2-methoxy-4-ethoxystyrylsulfone.

13. The method of claim 1 wherein the radioprotective compound is according to formula V:

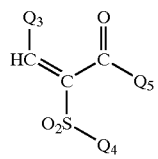

wherein
- $Q_3$, $Q_4$ and $Q_5$ are independently selected from the group consisting of phenyl and mono-, di-, tri-, tetra- and penta-substituted phenyl where the substituents, which may be the same or different, are independently selected from the group consisting of halogen, C1–C8 alkyl, C1–C8 alkoxy, nitro, cyano, carboxy, hydroxy, phosphonato, amino, sulfamyl, acetoxy, dimethylamino(C2–C6 alkoxy), C1–C6 trifluoroalkoxy and trifluoromethyl; or a pharmaceutically acceptable salt thereof.

14. The method of claim 13 wherein the radioprotective compound is according to formula Va:

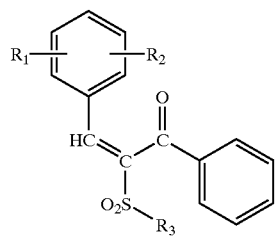

wherein
- $R_1$ and $R_2$ are independently selected from the group consisting of hydrogen, halogen, C1–C8 alkyl, C1–8 alkoxy, nitro, cyano, carboxy, hydroxy, and trifluoromethyl; and
- $R_3$ is selected from the group consisting of unsubstituted phenyl, mono-substituted phenyl and di-substituted phenyl, the substituents on the phenyl ring being independently selected from the group consisting of halogen and C1–8 alkyl; or a pharmaceutically acceptable salt thereof.

15. The method of claim 1, wherein the radioprotective compound is administered before exposure to the ionizing radiation.

16. The method of claim 15 wherein the radioprotective compound is administered at least about 6 hours before exposure to the ionizing radiation.

17. The method of to claim 16 wherein the radioprotective compound is administered no more than about 24 hours before exposure to the ionizing radiation.

18. The method of claim 15 wherein the radioprotective compound is administered about 18 hours and about 6 hours before exposure to the ionizing radiation.

19. The method of claim 1, wherein the radioprotective compound is administered after exposure to ionizing radiation.

20. The method of claim 19, wherein the radioprotective compound is administered between 0–6 hours after exposure to ionizing radiation.

21. A method of treating a subject with a proliferative disorder, comprising:
- (a) administering to the subject an effective amount of at least one radioprotective α,β unsaturated aryl sulfone compound; and
- (b) administering an effective amount of therapeutic ionizing radiation.

22. The method of claim 21 wherein the proliferative disorder is cancer.

23. A method of safely increasing the dosage of therapeutic ionizing radiation used in the treatment of cancer or other proliferative disorders, comprising administering an effective amount of at least one radioprotective α,β unsaturated aryl sulfone compound prior to administration of the therapeutic ionizing radiation, which radioprotective compound induces a temporary radioresistant phenotype in the normal tissue of the subject.

24. A method for treating a subject who has incurred or is at risk for incurring remediable radiation damage from exposure to ionizing radiation, comprising administering an effective amount of at least one radioprotective α,β unsaturated aryl sulfone compound prior to or after incurring remedial radiation damage from exposure to ionizing radiation.

25. The method of claim 21, 23 or 24, wherein the radioprotective compound is selected from the group consisting of (E)-4-fluorostyryl-4-chlorobenzylsulfone and (E)-4-carboxystyryl-4-chlorobenzylsulfone.

26. The method of claim 24 wherein the radioprotective compound is administered before incurring remedial radiation damage from exposure to ionizing radiation.

27. The method of claim 26, wherein the radioprotective compound is administered at least about 6 hours before incurring remedial radiation damage from exposure to ionizing radiation.

28. The method of claim 27 wherein the radioprotective compound is administered no more than 24 hours before incurring remedial radiation damage from exposure to ionizing radiation.

29. The method of claim 26, wherein the radioprotective compound is administered about 18 hours and about 6 hours before incurring remedial radiation damage from exposure to ionizing radiation.

30. The method of claim 24, wherein the radioprotective compound is administered after incurring remediable radiation damage from exposure to ionizing radiation.

31. The method of claim 30, wherein the radioprotective compound is administered between about 0–6 hours after incurring remediable radiation damage from exposure to ionizing radiation.

32. A method of reducing the number of malignant cells in bone marrow of a subject, comprising:
- (1) removing a portion of the subject's bone marrow;
- (2) administering an effective amount of at least one radioprotective α,β unsaturated arylsulfone to the bone marrow;
- (3) irradiating the bone marrow with an effective amount of ionizing radiation.

33. The method of claim 32, further comprising reimplanting the bone marrow into the subject.

34. The method of claim 32, wherein the subject receives therapeutic ionizing radiation prior to reimplantation of the bone marrow, and is administered one or more radioprotective α,β unsaturated arylsulfones prior to receiving the therapeutic ionizing radiation.

35. The method of claim 32 wherein the radioprotective compound is administered at least about 6 hours before exposure of the bone marrow to the ionizing radiation.

36. The method of to claim 32 wherein the radioprotective compound is administered about 20 hours before exposure to the ionizing radiation.

37. The method of claim 32 wherein the radioprotective compound is administered about 24 hours before exposure to the ionizing radiation.

38. The method of claim 2 wherein the substituents are selected from the group consisting of hydrogen, halogen, C1–C8 alkyl, C1–C8 alkoxy, nitro, cyano, carboxy, hydroxy, phosphonato, amino, sulfamyl, acetoxy, dimethylamino (C2–C6 alkoxy), C1–C6 trifluoroalkoxy and trifluoromethyl.

39. The method of claim 2 wherein the heteroaryl is selected from the group consisting of benzimidazolyl, benzofuryl, 2-benzothiazolyl, 5-benzothiazolyl, benzothienyl, 4-(2-benzyloxazolyl), furyl, isoquinolyl, isoxazolyl, imidazolyl, indolyl, oxazolyl, purinyl, pyrrolyl, pyrazolyl, pyrazinyl, pyridazinyl, pyridyl, pyrimidinyl, quinoxalinyl, quinolinyl, 5-tetrazolyl, thiazolyl, and thienyl.

40. The method of claim 39 wherein the benzimidazolyl is 2-benzimidazolyl, the benzofuryl is 3-, 4-, 5-, 6- and 7-benzofuryl, the benzothienyl is 3-, 4-, 5-, 6-, and 7-benzothienyl, the furyl is 2- and 3-furyl, the isoquinolyl is 1- and 5-isoquinolyl, the isoxazolyl is 3-, 4- and 5-isoxazolyl, the imidazolyl is 2-, -4 and 5-imidazolyl, the indolyl is 3-, 4-, 5-, 6- and 7-indolyl, the oxazolyl is 2-, 4- and 5-oxazolyl, the pyrrolyl is 2-pyrrolyl, and 3-pyrrolyl, the pyrazolyl is 3- and 5-pyrazolyl, the pyrazinyl is 2-pyrazinyl, the pyridazinyl is 3- and 4-pyridazinyl, the pyridyl is 2-, 3- and 4-pyridyl, the pyrimidinyl is 2- and 4-pyrimidyl, the quinoxalinyl is 2- and 5-quinoxalinyl, the quinolinyl is 2- and 3-quinolinyl, the thiazolyl is 2-thiazolyl, 4-thiazolyl and 5-thiazolyl, and thienyl is 2- and 3-thienyl, and 3-(1,2,4-triazolyl).

* * * * *